United States Patent
Sakurai et al.

(10) Patent No.: US 6,666,875 B1
(45) Date of Patent: Dec. 23, 2003

(54) SURGICAL APPARATUS PERMITTING RECHARGE OF BATTERY-DRIVEN SURGICAL INSTRUMENT IN NONCONTACT STATE

(75) Inventors: Tomohisa Sakurai, Sagamihara (JP); Shinji Hatta, Hachioji (JP); Akira Shiga, Hidaka (JP); Tsuyoshi Tsukagoshi, Fuchu (JP); Koji Yasunaga, Hino (JP); Masaru Karasawa, Yokohama (JP); Hiroyuki Sangu, Hino (JP); Takeaki Nakamura, Hino (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/492,711

(22) Filed: Jan. 27, 2000

(30) Foreign Application Priority Data

| Mar. 5, 1999 | (JP) | H11-059271 |
| Mar. 19, 1999 | (JP) | H11-076336 |
| Mar. 24, 1999 | (JP) | H11-080534 |
| Mar. 26, 1999 | (JP) | H11-084350 |
| Mar. 30, 1999 | (JP) | H11-089393 |

(51) Int. Cl.[7] .............................. A61B 17/32
(52) U.S. Cl. ................... 606/169; 30/DIG. 1
(58) Field of Search .............. 606/169; 623/3.27, 623/3.1; 607/151; 320/137; 30/DIG. 1

(56) References Cited

U.S. PATENT DOCUMENTS

| 3,867,950 A | * | 2/1975 | Fischell | 320/137 |
| 4,958,432 A | * | 9/1990 | Marshall | 30/29.5 |
| 5,129,789 A | * | 7/1992 | Thornton et al. | 417/322 |
| 5,544,382 A | * | 8/1996 | Giuliani et al. | 15/22.1 |
| 5,561,881 A | * | 10/1996 | Klinger et al. | 15/22.1 |
| 5,688,265 A | | 11/1997 | Citronowicz | 606/30 |
| 5,693,091 A | * | 12/1997 | Larson et al. | 623/3.27 |
| 5,727,273 A | * | 3/1998 | Pai | 15/22.1 |
| 5,994,855 A | * | 11/1999 | Lundell et al. | 318/114 |
| 6,048,345 A | * | 4/2000 | Berke et al. | 606/171 |
| 6,149,683 A | * | 11/2000 | Lancisi et al. | 600/16 |
| 6,235,027 B1 | * | 5/2001 | Herzon | 606/28 |

FOREIGN PATENT DOCUMENTS

JP 2-43501 9/1990

* cited by examiner

Primary Examiner—Michael J. Milano
Assistant Examiner—Bradford C Pantuck
(74) Attorney, Agent, or Firm—Ostrolenk, Faber, Gerb & Soffen, LLP

(57) ABSTRACT

A surgical instrument can be disinfected or sterilized, and has a rechargeable secondary battery incorporated therein. A distal treatment section of the surgical instrument is ultrasonically oscillated or otherwise activated using the secondary battery as a driving power source to perform surgery on a living tissue. Electromagnetic energy generated by an energy generation unit located outside the surgical instrument is received by a reception coil incorporated in the surgical instrument with the surgical instrument by induction from the energy generation unit. The electromagnetic energy is then converted into charging power with which the secondary battery is recharged. Thus, the surgical instrument can be readily recharged without compromising sterility.

25 Claims, 32 Drawing Sheets

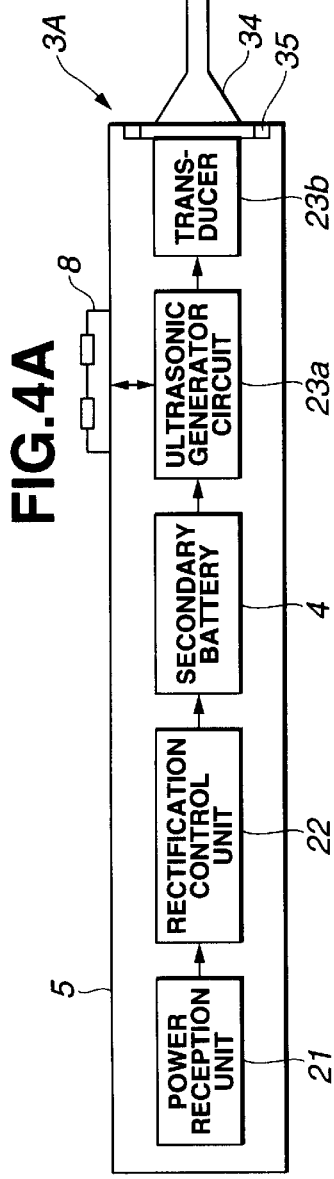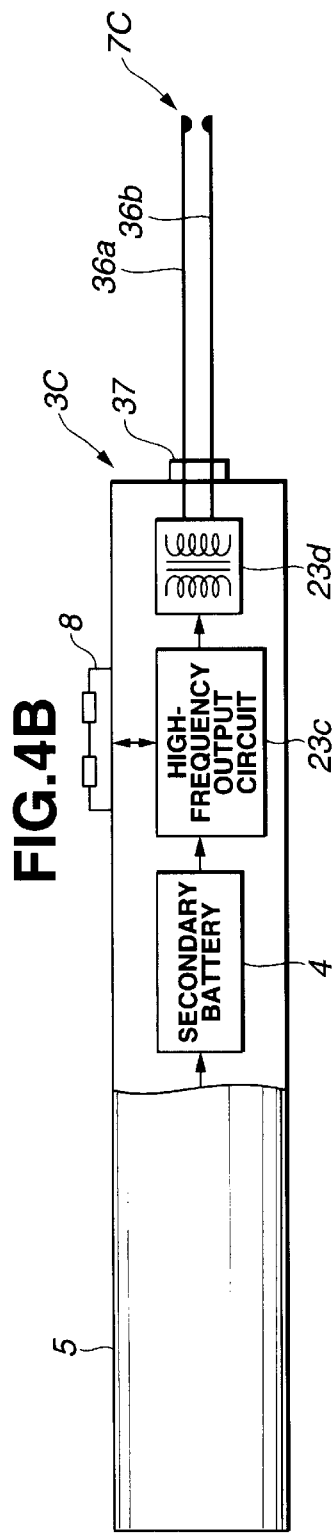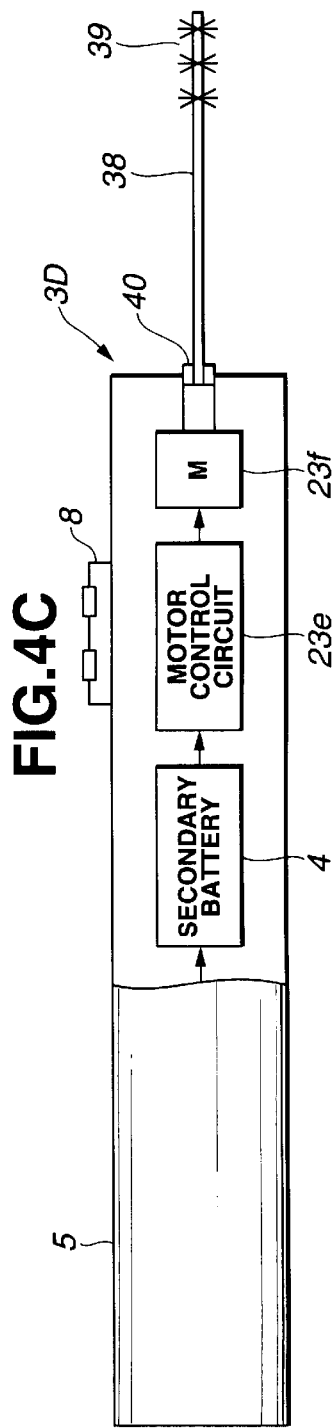

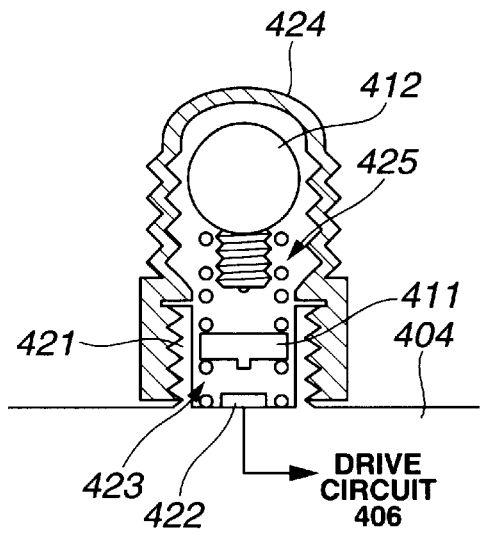
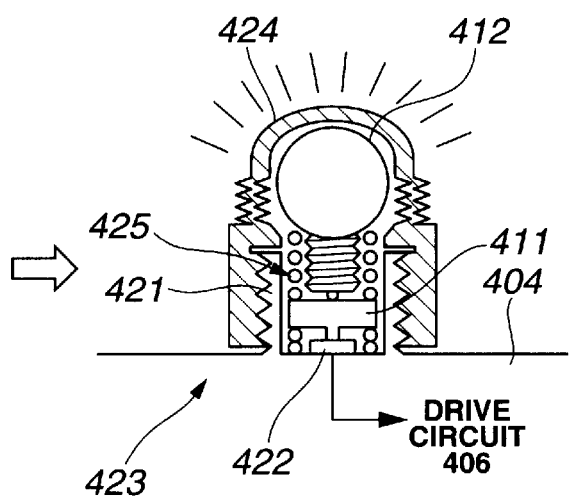
FIG.38A
FIG.38B
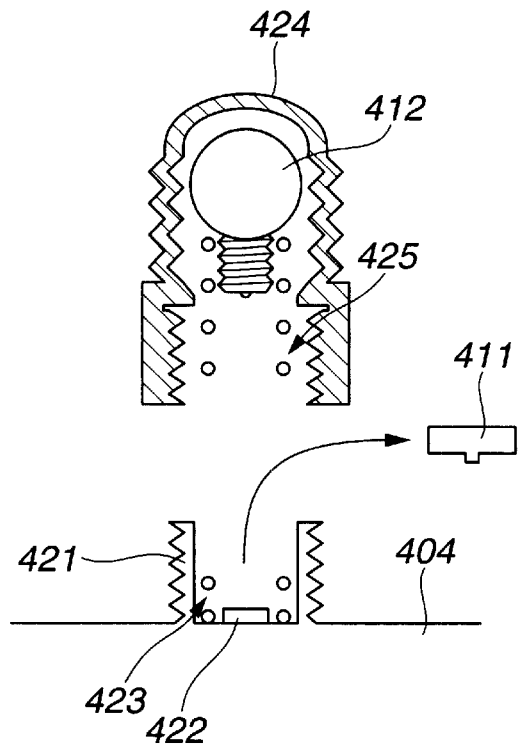
FIG.39

US 6,666,875 B1

SURGICAL APPARATUS PERMITTING RECHARGE OF BATTERY-DRIVEN SURGICAL INSTRUMENT IN NONCONTACT STATE

BACKGROUND OF THE INVENTION

1. Field of the Invention

The present invention relates to a surgical apparatus making it possible to recharge a secondary battery included in a battery-driven surgical instrument with an energy generation unit such as a recharger and the surgical instrument held in noncontact with each other.

2. Description of the Related Art

In recent years, surgical procedures to be performed under endoscopic observation have been developed.

A surgical instrument in accordance with a related art disclosed in, for example, Japanese Examined Patent Publication No. 2-43501 has a battery incorporated in a handpiece. Moreover, a motor and a treatment instrument are unified, and the motor is powered with the built-in battery.

According to the related art, the necessity of a power cord that is annoying an operator who manipulates the surgical instrument can be obviated to improve the maneuverability of the surgical instrument. There is a drawback that when electrical energy contained in the battery runs out, treatment cannot be performed any longer.

To avoid having to replace the battery during surgery it must be done prior to the surgery. However, this is added work, and if the surgical instrument has merely been used at some steps of a surgical procedure, there is a possibility that the battery need not be renewed. Nevertheless, to avoid the trouble of renewing the battery during surgery, the battery is replaced beforehand.

Moreover, when replacing a battery in a sterilized surgical instrument, the surgical instrument must be handled very carefully for fear it may be contaminated. A nurse or the like is obliged to incur a large burden.

For overcoming this drawback, a rechargeable battery may be incorporated in the surgical instrument and recharged using a recharger. However, the related art has a drawback that the sterilized surgical instrument must be sterilized again or must be handled carefully so as not to be contaminated during connection of the recharger. Moreover, measures must be taken to maintain the watertightness of the junction between the surgical instrument and recharger.

SUMMARY OF THE INVENTION

An object of the present invention is to provide a surgical apparatus making it possible to recharge a sterilized surgical instrument without risk of contamination.

Another object of the present invention is to provide a surgical apparatus substantially obviating the necessity of renewing a battery during surgery.

A surgical apparatus according to the invention is comprised of a surgical instrument, an energy generation unit, an energy radiating device, and a charging energy producing device. The surgical instrument has a rechargeable secondary battery and a treatment section to be electrically driven by the secondary battery, and can be disinfected or sterilized. The energy generation unit is located outside the surgical instrument and used to recharge the secondary battery. The energy radiating device included in the energy generation unit radiates energy. The charging energy producing device is incorporated in the surgical instrument, receives energy without the need for the surgical instrument and energy generation unit to be in contact with each other, and produces energy used to recharge the secondary battery.

Consequently, the secondary battery can be recharged without the sterilized surgical instrument being contaminated. Moreover, the recharge substantially obviates the necessity of renewing the battery during surgery.

BRIEF DESCRIPTION OF THE DRAWINGS

FIG. 1 to FIG. 5B relate to the first embodiment of the present invention;

FIG. 1 shows the configuration of a surgical system including the first embodiment;

FIG. 2 shows the configuration of the surgical system being recharged;

FIG. 4A to FIG. 4C are block diagrams showing examples of the configurations of surgical instruments;

FIG. 5A and FIG. 5B show the electrical systems of a surgical instrument and a recharger in accordance with a variant;

FIG. 6 is a sectional diagram showing the configuration of a surgical instrument employed in the second embodiment;

FIG. 7 is a circuit diagram showing the electrical system of the surgical instrument;

FIG. 8 shows the appearance of a surgical system having the third embodiment;

FIG. 9 shows the configuration of part of the surgical system shown in FIG. 8;

FIG. 10 shows the appearance of a surgical apparatus in accordance with the fourth embodiment;

FIG. 11 shows the internal configurations of a surgical instrument and a recharger;

FIG. 12 is a sectional view showing a recharge receptacle freely attachable or detachable to or from the recharger;

FIG. 14 shows the appearance of an ultrasonic treatment instrument in accordance with the sixth embodiment;

FIG. 15 details the configuration of the ultrasonic treatment instrument shown in FIG. 14;

FIG. 16 shows the configuration of an output adjustment mechanism included in the ultrasonic treatment instrument;

FIG. 17 shows an output adjustment mechanism in accordance with a variant;

FIG. 19 shows the configuration of an output adjustment mechanism included in a high-frequency treatment instrument in accordance with the eighth embodiment;

FIG. 20 shows the configuration of a strain detection device;

FIG. 21 shows the appearance of an ultrasonic treatment instrument in accordance with the fourth embodiment;

FIG. 22 shows the configuration of the major portion of the ultrasonic treatment instrument;

FIG. 25 is an oblique view showing the appearance of an ultrasonic coagulation/incision instrument in accordance with the twelfth embodiment;

FIG. 26 is an explanatory diagram showing the internal configuration of the ultrasonic coagulation/incision instrument shown in FIG. 25;

FIG. 27 is an explanatory diagram showing another example of the ultrasonic coagulation/incision instrument;

FIG. 30 shows the configuration of a battery-powered ultrasonic coagulation/incision instrument in accordance with the fifteenth embodiment;

FIG. 31 shows the configuration of a drive circuit shown in FIG. 30;

FIG. 32 shows the relationship between an amount of energy output from a control circuit shown in FIG. 31 to a drive unit and the frequency of an output sound of a buzzer;

FIG. 33 shows the first example of a cylinder shown in FIG. 30;

FIG. 34 shows the second example of the cylinder shown in FIG. 30;

FIG. 36 to FIG. 39 relate to the seventeenth embodiment of the present invention;

FIG. 36 shows the configuration of a surgical instrument in accordance with the seventeenth embodiment;

FIG. 37 shows a conducting state of a battery unit shown in FIG. 36;

FIG. 38A and FIG. 38B details the configuration of the battery unit shown in FIG. 37;

FIG. 39 is an explanatory diagram concerning renewal of a battery in the battery unit;

DESCRIPTION OF THE PREFERRED EMBODIMENTS

Embodiments of the present invention will be described with reference to the drawings below.

First Embodiment

Figure 1:
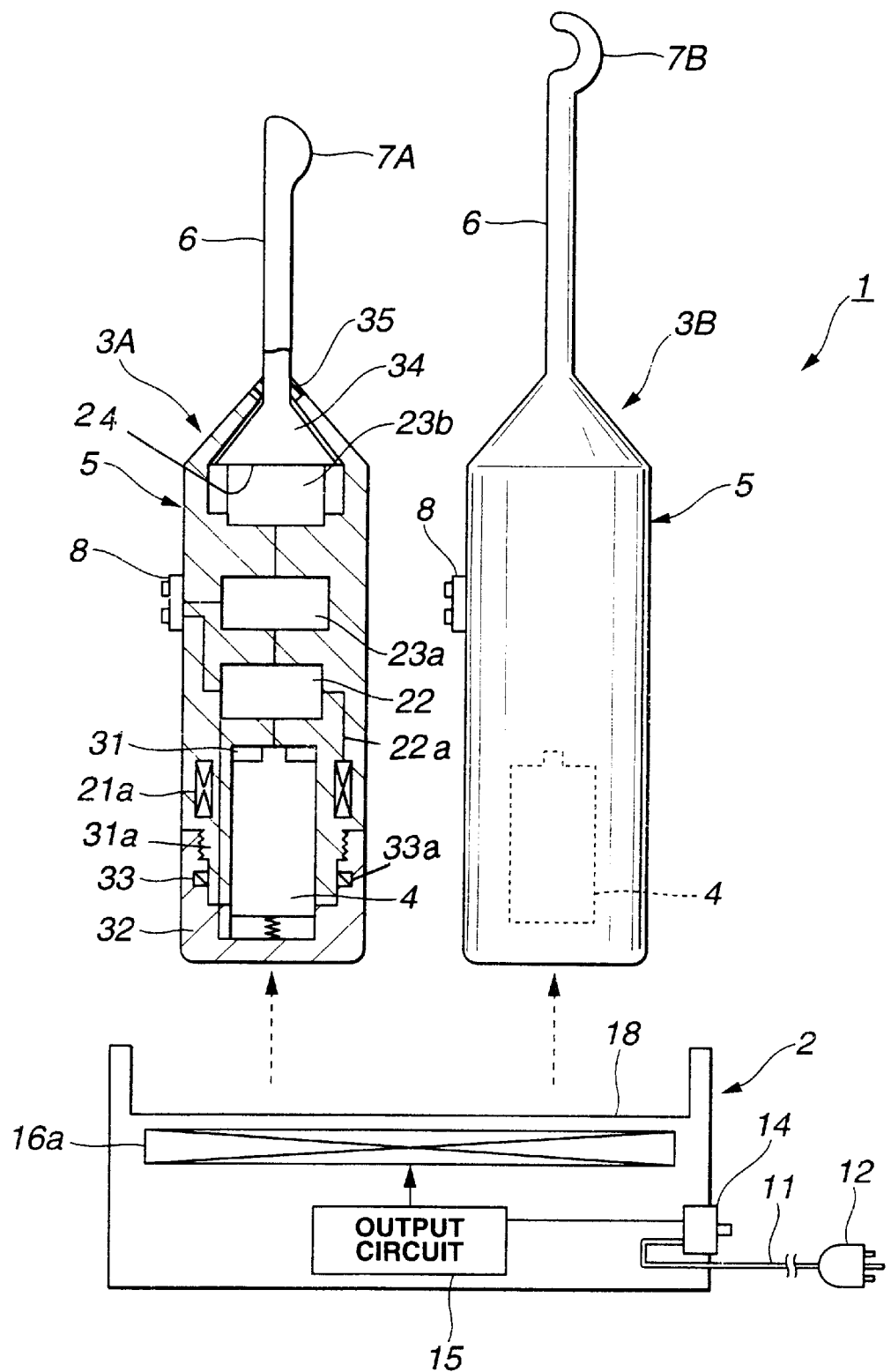
Figure 2:
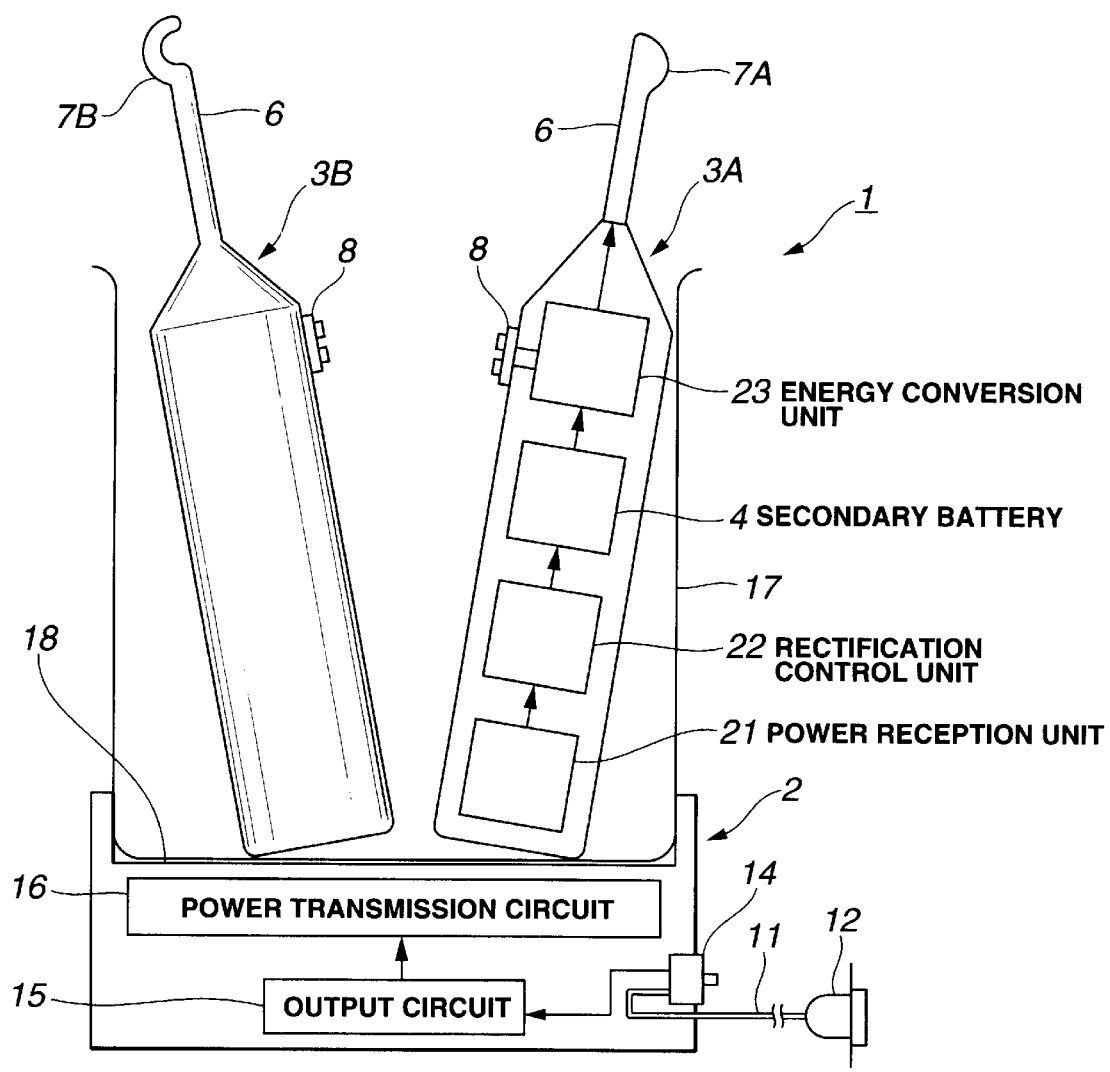

An surgical system 1 according to the first embodiment as shown in FIG. 1 and FIG. 2, is comprised of a recharger 2 and a surgical instrument 3A or 3B. The recharger 2 serves as an energy generation unit and is constructed to generate energy used for recharge and radiate the energy. The surgical instrument 3A or 3B is used to perform surgery (treatment) on a living body for cure. A charging energy producing device described below which receives energy from the recharger 2, and a rechargeable secondary battery 4 is incorporated in the surgical instrument 3A or 3B.

Surgical instrument 3A or 3B further include a hand-held portion 5 held by an operator and a shaft portion 6 extending out of the hand-held portion 5. A treatment section 7A or 7B used to treat a living tissue or the like is formed as the distal part of the shaft portion 6.

The hand-held portion 5 has a switch 8. The switch 8 is turned on or off for activating or deactivating treatment section 7A or 7B.

Recharger 2 has a power cord 11 to be plugged into the mains. A plug 12 attached to the distal end of the power cord 11 is fitted into a mains receptacle, whereby alternating electrical energy is supplied from the mains to an output circuit 15 via a power switch 14.

The output circuit 15 converts the alternating electrical energy into, electrical energy of a higher frequency. The output circuit 15 is connected to a power transmission circuit 16 including a power transmission coil 16a.

Figure 3A:
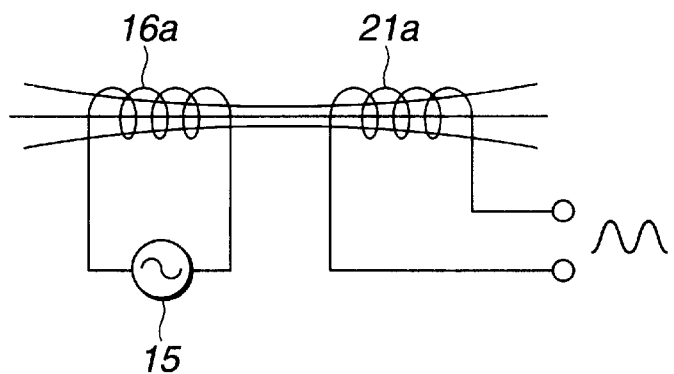
FIG. 3A to FIG. 3C show the principles of operation for noncontact recharge and the electrical systems of a surgical instrument and a recharger.
Figure 3B:
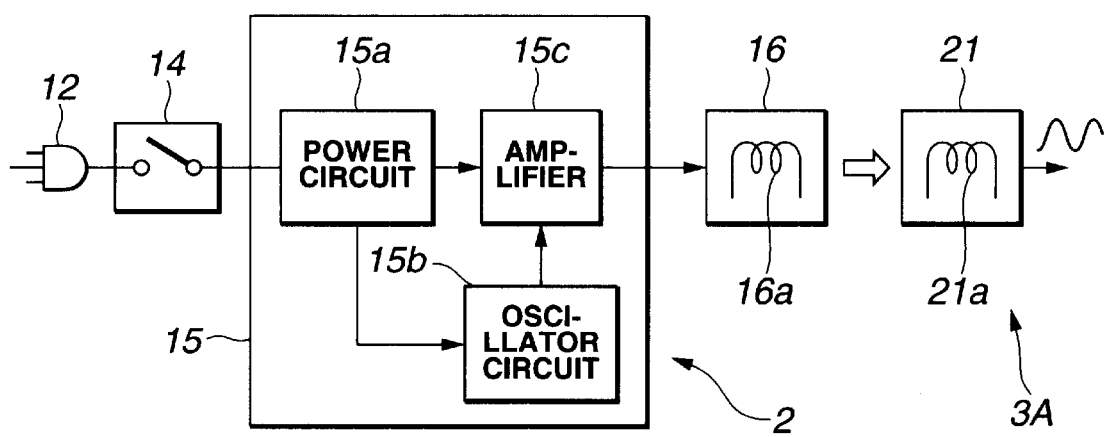

The output circuit 15 may include, as shown in FIG. 3B, a power circuit 15a, an oscillator circuit 15b, and an amplifier 15c. The oscillator circuit 15b oscillates with direct voltage produced by the power circuit 15a. Direct current is supplied from the power circuit to the amplifier 15c that amplifies an oscillating signal output from the oscillator circuit 15b. The power transmission coil 16a included in the power transmission circuit is connected to the output terminal of the amplifier 15c.

The oscillator circuit 15b oscillates at frequencies ranging from, for example, several kilohertz to several megahertz. The high-frequency signal is amplified by the amplifier 15c and sent to the power transmission coil 16a serving as a power transmitting means.

Then, electromagnetic energy is radiated from the power transmission coil 16a to the surroundings.

As shown in FIG. 2, a concave vial placement section 18 is formed on the top of the recharger 2. A vial 17 in which the clean surgical instruments 3A and 3B that have been washed and disinfected (or sterilized) is put is placed on the vial placement section 18. The vial 17 can be washed and disinfected (or sterilized).

The body of recharger 2 having the power transmission coil 16a embedded therein, and the vial 17 are made of a material transparent to electromagnetic energy, for example, a glass or a resin such as Teflon.

The surgical instruments 3A and 3B are put in the clean vial 17. Secondary batteries 4 in the surgical instruments 3A and 3B are recharged from the recharger 2 by the energy radiated by power transmission coil 16a.

Specifically, with surgical instruments 3A and 3B are held separated from the recharger 2 in vial 17, electromagnetic energy used for recharge is supplied to power reception units 21, which are incorporated in the surgical instruments 3A and 3B, via the vial 17.

As shown in FIG. 2, surgical instrument 3A is comprised of the power reception unit 21, a rectification control unit 22, the secondary battery 4, an energy conversion unit 23, and the treatment section 7A. The power reception unit 21 receives electromagnetic energy radiated from the power transmission circuit 16. The rectification control unit 22 converts the electromagnetic energy received by the power reception unit 21 into direct current and adjusts the voltage to a level suitable for recharging the secondary battery 4. The battery may be comprised of nickel-hydrogen cells, nickel-copper cells or the like that are rechargeable with an output of the rectification control unit 22.

The energy conversion unit 23 is driven by the secondary battery 4. The treatment section 7A, for example, a knife, may be driven directly by the energy conversion unit 23 or via the shaft portion 6 serving as a propagation member.

Figure 3C:
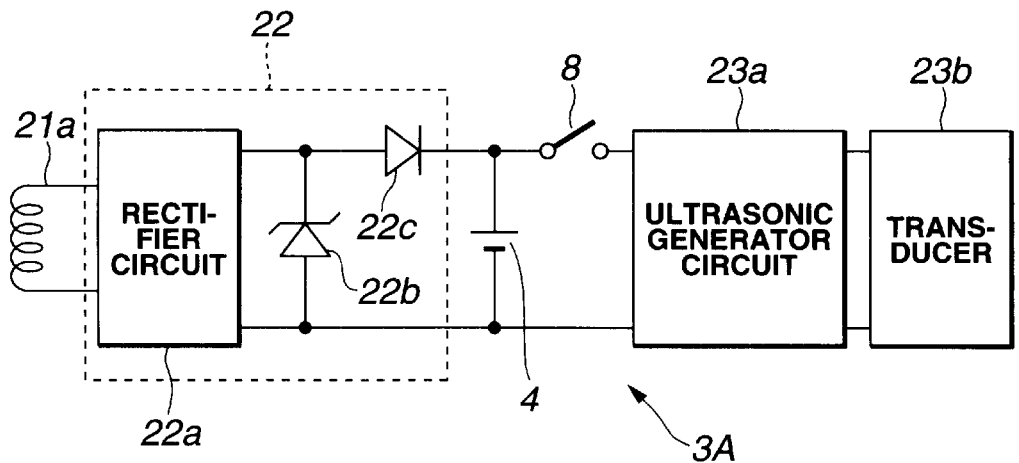

When the surgical instrument 3A is, for example, an ultrasonic knife, the energy conversion unit 23 is, as shown in FIGS. 3C and 4A, comprised of an ultrasonic generator circuit 23a and an ultrasonic transducer 23b.

FIG. 1 shows a practical configuration of a surgical instrument such as an ultrasonic knife.

The surgical instrument 3A has a battery chamber 31 near the back end of the hand-held portion 5. The back end 31a of the battery chamber 31 is open, and terminates in a threaded portion which mates with a threaded lid 32. A seal such as an O ring 33 is located in a groove 33a in lid 32. When the lid 32 is engaged with the battery chamber 31, the interior of the battery chamber can thus be held watertight.

A power reception coil 21a included in the power reception unit 21 is wound about the battery chamber 31. Electrical energy induced in the power reception coil 21a is input to the rectification control unit 22 over a lead 22a. The rectification control unit 22 adjusts an amount of electrical energy according to voltage suitable for recharging the secondary battery 4 and supplies the electrical energy to the battery.

The secondary battery 4 is connected to the ultrasonic generator circuit 23a via the switch 8. The ultrasonic transducer 23b is connected to the output terminal of the ultrasonic generator circuit 23a. When an output signal of the ultrasonic generator circuit 23a is applied to the ultrasonic transducer 23b, the ultrasonic transducer 23b oscillates at an ultrasonic frequency.

In FIG. 1, the power reception coil 21a, rectification control unit 22, and ultrasonic generator circuit 23a are embedded in an insulating member.

The front end 24 of the ultrasonic transducer 23b is connected to the shaft portion 6 through an intermediate horn 34. Ultrasonic waves generated by the ultrasonic transducer 23b are amplified by the horn 34, and propagated into the distal treatment section 7A by way of the shaft portion 6.

The junction between the front end of the horn 34 and the shaft portion 6 is shielded with a cover member (armor member) covering the hand-held portion 5 via a seal member 35 such as a rubber member. The interior of the hand-held portion 5 is held watertight so that the hand-held portion 5 can not only be washed with a cleaning solvent but also be disinfected (or sterilized) with a disinfectant (or a sterilant). Moreover, the hand-held portion 5 resists sterilization to be performed using a sterilization gas.

Shaft portion 6 may be sealed at the proximal end of the horn 34 as shown in FIG. 4A.

FIG. 3C shows a practical example of the electrical system of the surgical instrument 3A.

Specifically, the power reception coil 21a has both ends thereof connected to input terminals of a rectifier circuit 22a included in the rectification control unit 22. After alternating current is rectified and smoothed, the resultant current is stabilized by a constant-voltage diode 22b so that constant voltage will be developed at the secondary battery. The constant-voltage diode 22b is connected to the secondary battery 4 via an anti-reverse flow diode 22c.

The secondary battery 4 has one terminal thereof connected directly to an input terminal of the ultrasonic generator circuit 23a. The other terminal of the secondary battery 4 is connected to the input terminal of the ultrasonic generator circuit via the switch 8. The ultrasonic transducer 23b is connected to the output terminals of the ultrasonic generator circuit 23a.

The surgical instrument 3B has the same configuration as the surgical instrument 3A except that the shaft portion 6 thereof is longer than that of the surgical instrument 3A and that the distal treatment section 7B thereof is shaped like, for example, a hook. The surgical instrument 3B can be disinfected in the same manner as the surgical instrument 3A.

Surgical instruments 3A and 3B have been described as ultrasonic knives. Alternatively, the surgical instrument 3A or 3B may be an electric cauterizer 3C as shown in FIG. 4B, or may be a motor-driven treatment instrument 3D as shown in FIG. 4C.

As shown in FIG. 4B, the electric cauterizer 3C has a high-frequency output circuit 23c in place of the ultrasonic generator circuit included in the ultrasonic knife 3A. The high-frequency output circuit 23c oscillates at a high frequency. An oscillating output of the high-frequency output circuit is amplified and output. The output terminal of the high-frequency output circuit 23c is connected to the primary winding of an output transformer 23d. A high-frequency output signal is supplied to the secondary winding thereof isolated from the primary winding.

A pair of high-frequency electrodes 36a and 36b is connected to the secondary winding of the output transformer 23d. A high-frequency output signal is transmitted to the treatment section 7C is located distally to the high-frequency electrodes. The treatment section 7C is brought into contact with a living tissue to be treated, whereby resection or cauterizer can be achieved.

A section of the hand-held portion 5 from which the high-frequency electrodes 36a and 36b extend is sealed to be watertight and airtight using an insulating member 37.

The motor-driven treatment instrument 3D shown in FIG. 4C has a motor control unit 23e in place of the ultrasonic generator circuit 23a included in the ultrasonic knife 3A shown in FIG. 4A. A motor 23f is driven to rotate with an output signal of the motor control unit 23e.

A shaft portion 38 extending from the hand-held portion 5 is coupled to the axis of rotation of the motor 23f. A rotary brush 39, for example, may be formed as a treatment section in the distal part of the shaft portion 38. The rotary brush 39 is used to peel off surface tissue or perform any other treatment.

A seal member 40 such as an O ring is put on a section of the hand-held portion 5 from which the shaft portion 38 extends, whereby watertightness is maintained.

Operations to be exerted by the first embodiment having the foregoing components will be described below.

For performing surgery using the surgical instruments 3A and 3B shown in FIG. 1, the lid 32 is opened in order to stow the secondary battery 4 in the battery chamber 31. The lid 32 is then closed. At this time, the surgical instruments 3A and 3B are held watertight and airtight, and can therefore be washed and disinfected (or sterilized).

The surgical instruments 3A and 3B are then washed and disinfected (or sterilized), and put in the vial 17 placed on the vial placement section 18 on the top of the recharger 2. The vial 17 has been washed and disinfected (or sterilized).

The plug 12 of the recharger 2 is fitted into a mains receptacle, and the switch 14 is turned on. Consequently, an oscillating signal output from the oscillator circuit 15b included in the output circuit 15 of the recharger 2 shown in FIG. 3B is amplified by the amplifier 15c, and applied to the power transmission coil 16a. An A.C. electromagnetic field is produced around the power transmission coil 16a. The electromagnetic field induces A.C. current flow in power reception coil 21a. Thus, energy is propagated to the power reception coil 21a without the need for a conductive connection with the power transmission coil.

As shown in FIG. 3C, the high-frequency signal produced by the power reception circuit 21a is supplied to the rectification control unit 22, rectified by the rectifier circuit 22a, and adjusted so that a voltage suitable for recharge will be developed at the secondary battery. The resultant signal is applied to the secondary battery 4, whereby the secondary battery 4 is recharged.

When the time required for recharge elapses, surgery can be performed using the secondary battery 4. An operator picks up, for example, the surgical instrument 3A from the vial 17, holds the hand-held portion 5, and presses an On switch of the switch 8. Driving power is then supplied from the secondary battery 4 to the ultrasonic generator circuit 23a. The ultrasonic generator circuit 23a in turn produces oscillations at an ultrasonic frequency. The ultrasonically oscillating output of the ultrasonic generator circuit is applied to the ultrasonic transducer 23b. This causes the ultrasonic transducer to oscillate at the ultrasonic frequency. The ultrasonic waves are propagated to the distal treatment section 7A by way of the shaft portion 6. This brings the treatment section 7A into contact with a living tissue. Consequently, resection or any other treatment is carried out.

After use, the surgical instrument 3A is washed and disinfected (or sterilized), put in the vial 17 again, and recharged.

Owing to the foregoing components, the secondary battery 4 incorporated in the surgical instrument 3A is recharged so that the surgical instrument 3A can be reused repeatedly. The surgical instrument 3A or the like must be washed and sterilized prior to every use. The recharger 2 is unclean. The vial 17 that has been washed and sterilized in advance is placed on the recharger 2. The surgical instrument 3A or the like is then put in the vial 17. Thus, the surgical instrument 3A or the like that has been sterilized can be recharged without risk of contamination.

If the number of times by which the secondary battery 4 is recharged reaches a limit due to repeated use, the secondary battery 4 may be replaced with a new one.

Figure 5A:
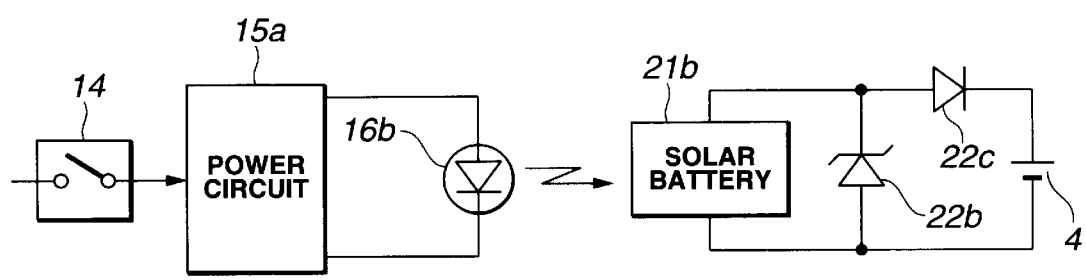
Figure 5B:
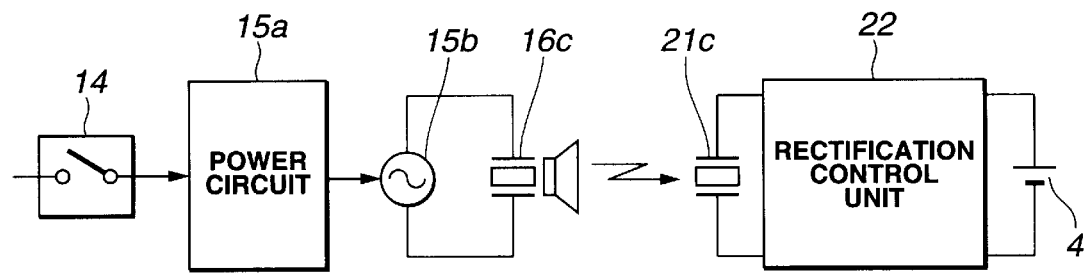

FIGS. 5A and 5B show energy propagating devices.

Referring to FIG. 5A, a light-emitting device such as a light-emitting diode (LED) 16b is caused to glow using a direct-current power source that is the power circuit 15a. Light emitted from the LED 16b is received by a photoelectric converter such as a solar battery 21b, whereby electromotive force causing direct current to flow is induced. The electromotive force is applied to the secondary battery 4 via a control unit comprised of a constant-voltage diode 22b and anti-reverse flow diode 22c.

In this case, a light-emitting section of the recharger 2 above the LED 16b as well as the vial 17 should be made of a material transparent to light, such as, a glass. Moreover, the solar battery 21 is embedded in the back end of the surgical instrument, for example, in the lid 32 so that the light-receiving section of the solar battery 21 will be opposed to the outer surface of the surgical instrument.

Referring to FIG. 5B, the oscillator circuit 15b is oscillated using a direct-current source that is the power circuit 15a. An oscillating output of the oscillator circuit causes a sound travelling device such as an ultrasonic loudspeaker 16c to output acoustic energy such as ultrasonic energy. An ultrasonic microphone 21c or the like receives the acoustic energy and converts it into electrical energy. The electrical energy is supplied to the secondary battery 4 via the rectification control unit 22. The secondary battery 4 may thus be recharged.

The present embodiment provides advantages described below.

According to the present embodiment, the secondary battery 4 incorporated in the battery-driven surgical instrument 3A or the like is recharged repeatedly. This makes the surgical instrument 3A or the like reusable many times. Contacts that are electrically coupled to each other are not needed for recharging the battery. The secondary battery can be recharged while held in noncontact with an unclean recharger. Consequently, the secondary battery can be recharged with the surgical instrument left sterilized.

In short, the surgical instrument will not be contaminated but be recharged readily. The recharge work is simplified greatly, and recharge control is simplified.

Since recharge is thus achieved, the trouble that a battery is exhausted during surgery (electrical energy runs short) and other troubles can be avoided.

Second Embodiment

Next, the second embodiment of the present invention will be described with reference to FIG. 6 and FIG. 7. The present embodiment is identical to the first embodiment except that a device for indicating that recharge is completed is in the surgical instrument 3A of the first embodiment.

Figure 6:
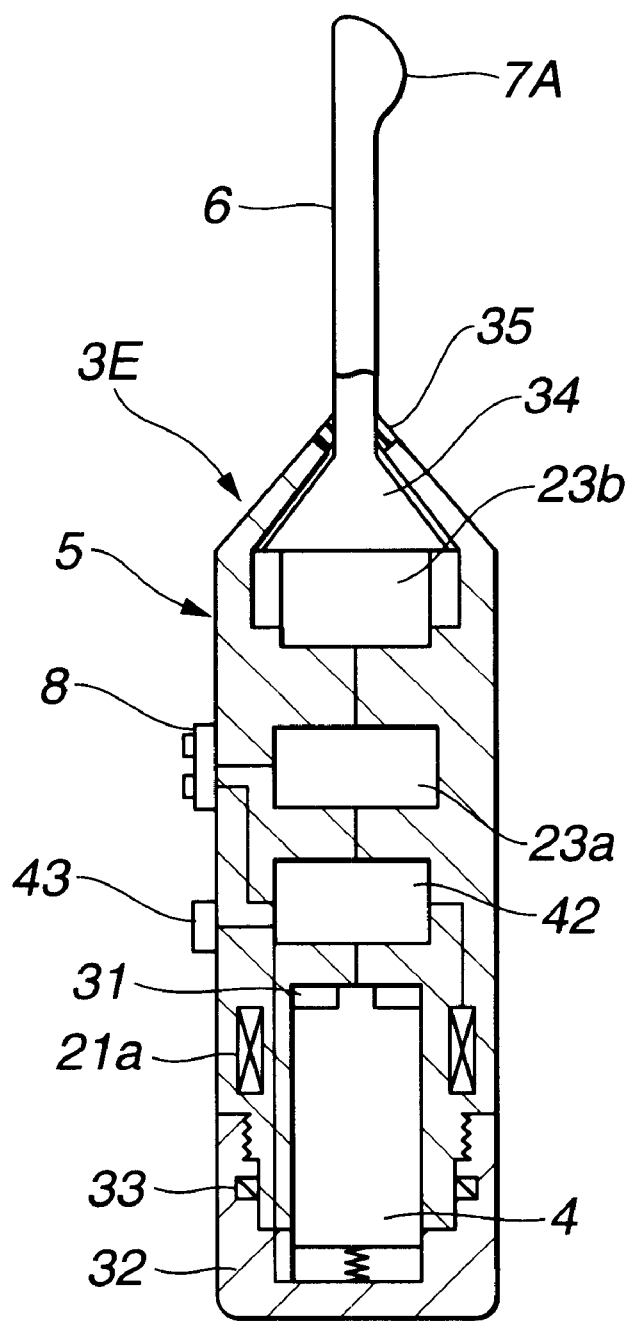
FIG. 6 and FIG. 7 relate to the second embodiment of the present invention.

FIG. 6 shows a surgical instrument 3E in accordance with this embodiment. The surgical instrument 3E will be described in comparison with the surgical instrument 3A shown in FIG. 1. Namely, instead of the rectification control unit 22, a rectification control judgment unit 42 formed by adding a recharged state judgment block 41 to the rectification control unit 22 is included in the hand-held portion 5. A recharge completion indicator LED 43 connected to the rectification control judgment unit 42 is mounted on the outer surface of the hand-held portion 5.

Figure 7:
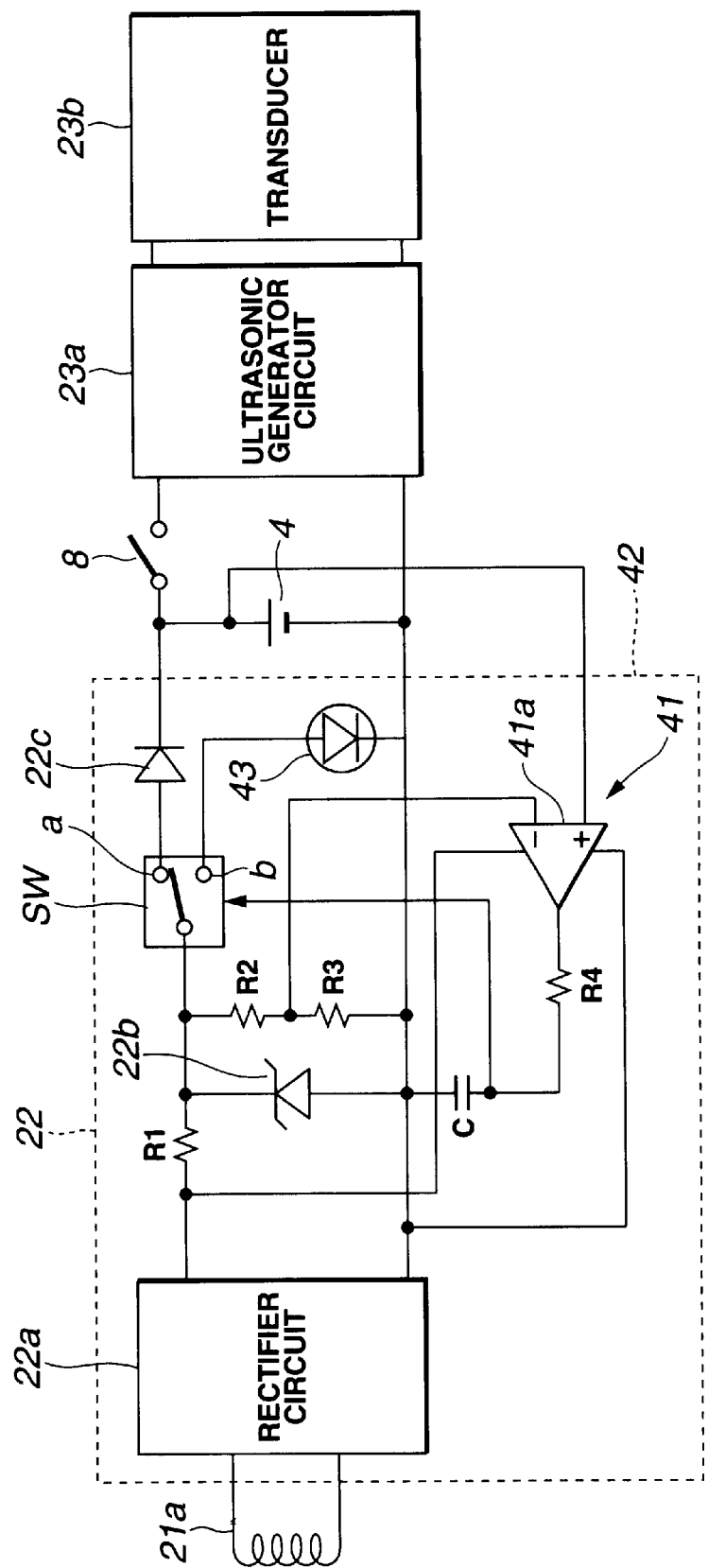

FIG. 7 shows the electrical system of the surgical instrument 3E. As shown in FIG. 7, the output terminals of the rectifier circuit 22a are connected to the positive and negative power terminals of a comparator 41a included in the recharged state judgment block 41. A constant-voltage diode 22b is connected to the rectifier circuit 22a via a current limiting resistor R1.

The cathode of the constant-voltage diode 22b is connected to the anode of the secondary battery 4 via a selection switch SW and the anti-reverse flow diode 22c.

The anode voltage of the secondary battery 4 is applied to the noninverting input terminal of the comparator 41a. A voltage stabilized by the constant-voltage diode 22b is lowered at resistors R2 and R3. A resultant reference voltage is applied to the inverting input terminal of the comparator 41a.

A resistor R4 and a capacitor C are connected to the output terminal of the comparator 41a. When the voltage at the secondary battery 4 exceeds the reference voltage, a voltage applied to charge the capacitor C is used to change the selection switch SW from a contact a to a contact b. Consequently, the LED 43 connected to the contact b is allowed to glow.

Incidentally, the resistances given by the resistors R2 and R3 are determined so that a voltage developed at the secondary battery 4 will be equal to the reference voltage at the completion of recharge.

Moreover, the selection switch SW is formed with, for example, an analog switch. The selection switch SW is, similarly to the comparator 41, powered by the rectifier circuit 22a (omitted from FIG. 7 for brevity's sake). The other components are identical to those of the first embodiment.

The present embodiment operates in the same manner as the first embodiment. In addition, when recharging the secondary battery is completed, the fact is detected by checking if the voltage at the secondary battery has exceeded the reference voltage. The contacts of the selection switch SW are then changed to prevent charging current from flowing into the secondary battery 4. Besides, the LED 43 is allowed to glow (lit).

When the LED 43 is lit, an operator recognizes that recharging the surgical instrument 3E has been completed. The operator should use a surgical instrument whose LED 43 is lit. It can thus be reliably prevented that a battery is exhausted during surgery.

The present embodiment can provide the same advantages as the first embodiment. In addition, by checking if the LED 43 is lit (or unlit), it can be recognized whether recharging the secondary battery 4 has been completed. Moreover, excessive recharge can be prevented, thereby lengthening the service life of the secondary battery 4.

In the present embodiment, a detecting means is included for detecting whether recharge is completed. When completion of recharge is detected, the LED 43 is lit in order to notify a user of completion of recharge. Alternatively, the LED 43 may be lit during recharge. When recharge is completed, the LED 43 may be put out. Whether recharge is in progress or completed may thus be notified.

For charging indication, the anode of the LED 43 shown in FIG. 7 is connected together with the anode of the diode 22c to the contact a of the selection switch SW. When recharge is in progress, a dedicated LED may be lit. When recharge is completed, the LED 43 for emitting light whose wavelengths are different from those of light emitted from the LED may be lit. Whether recharge is in progress or completed may thus be notified.

In this case, the LED 43 shown in FIG. 7 is realized with an LED that glows in green. To indicate charging, the cathode and anode of another LED that glows in red are connected to the cathode of the LED 43 and the contact a of the selection switch SW that are shown in FIG. 7.

Third Embodiment

A third embodiment of the present invention will be described with reference to FIG. 8 and FIG. 9.

Figure 8:
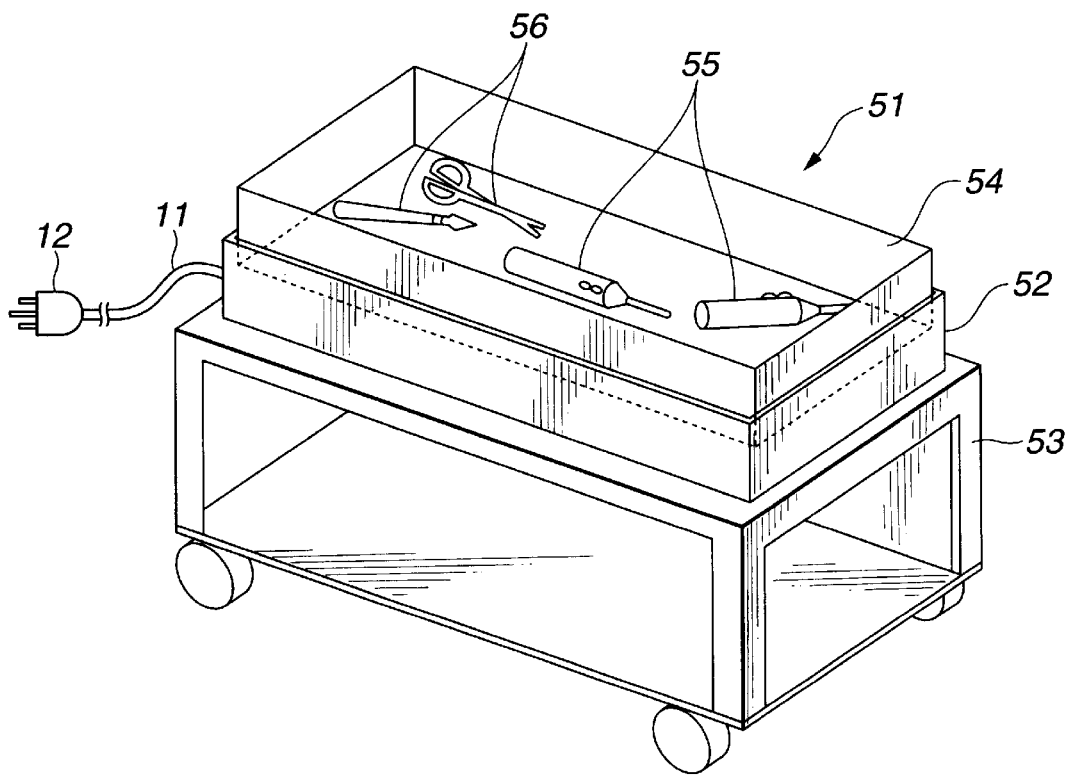
FIG. 8 and FIG. 9 relate to the third embodiment of the present invention.
Figure 9:
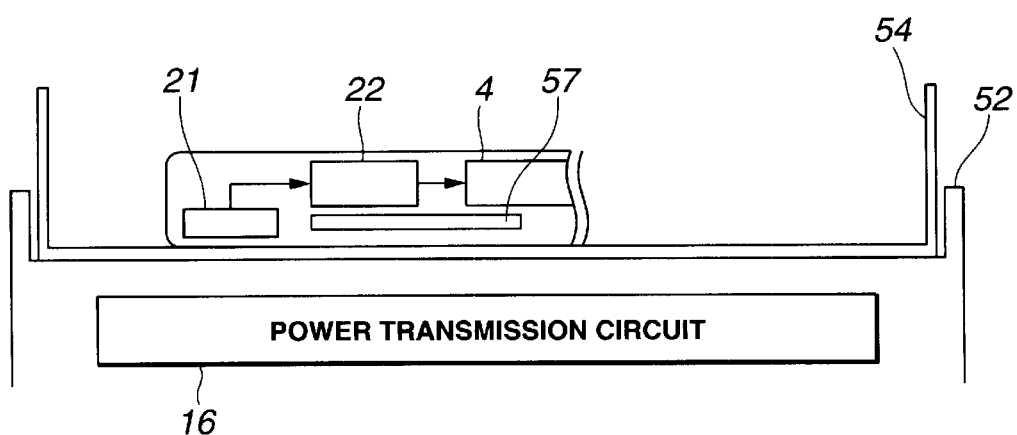

FIG. 8 shows a tray-like surgical system 51. The surgical system 51 consists of a recharger 52, a cart 53 on which the recharger 52 is placed, a sterilization tray 54 placed on the recharger 52. One or more battery-driven surgical instruments 55 may be placed in the sterilization tray 54, along with ordinary surgical instruments 56.

A cord 11 is extended from the recharger 52, and a plug 12 is attached to the distal end of the cord 11.

The recharger 52 has the same components as that in the first embodiment. The power transmission circuit 16 is, as shown in FIG. 9, included for supplying energy to the power reception units 21 incorporated in the battery-driven surgical instruments 55 placed on the recharger 52. At this time, the power transmission circuit 16 is in noncontact with the power reception units 21. Energy received by the power reception unit 21 is supplied to the secondary battery 4 via the rectification control unit 22. The secondary battery 4 is thus recharged.

When the surgical system is of the tray type, the surgical instruments 55 can be freely oriented in any direction. A weight 57 is therefore incorporated in each battery-driven surgical instrument 55, so that the power transmission circuit 16 and power reception unit 21 will be oriented so properly as to efficiently transmit energy. For example, when the power transmission circuit 16 and power reception unit 21 are formed with coils, they are oriented so that the axial directions of the coils will be parallel to each other. Thus, energy generated by the coil of the power transmission circuit 16 can be received efficiently by the coil of the power reception unit 21.

According to the third embodiment, the surgical instruments 55 oriented freely are put in the large sterilization tray 54. Nevertheless, the surgical instruments are recharged reliably.

Similarly to the second embodiment, when recharging the secondary battery 4 is completed, charging current may be prevented from flowing into the secondary battery 4. The LED 43 or the like maybe used to notify a user of the completion of recharge.

Fourth Embodiment

Figure 12:
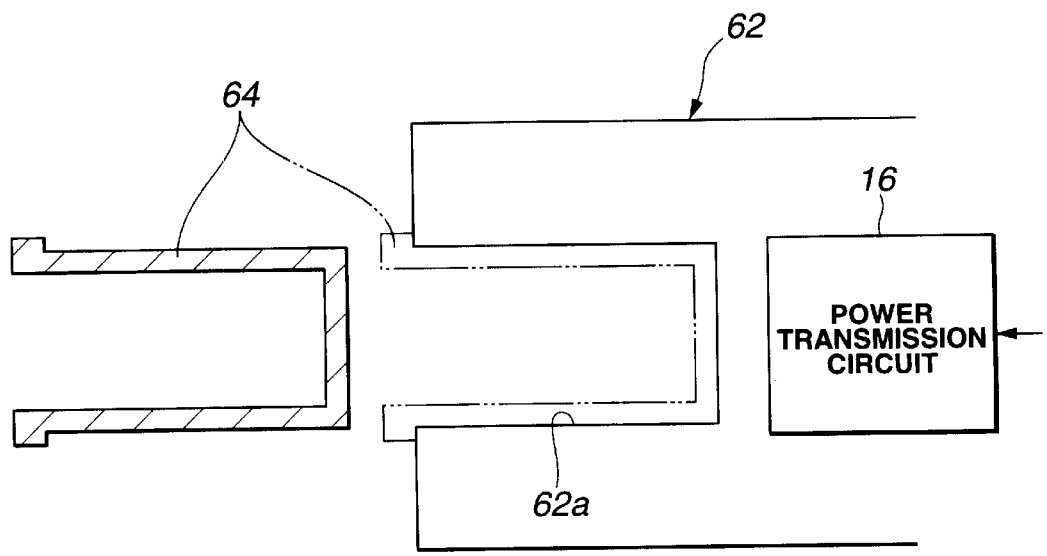

Next, the fourth embodiment of the present invention will be described with reference to FIG. 10 to FIG. 12.

Figure 10:
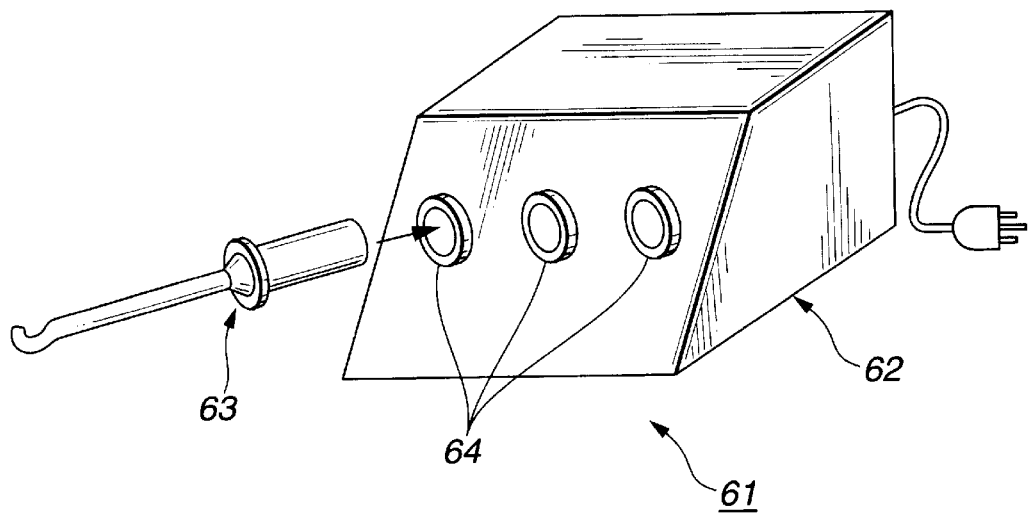
FIG. 10 to FIG. 12 relate to the fourth embodiment of the present invention.
Figure 11:
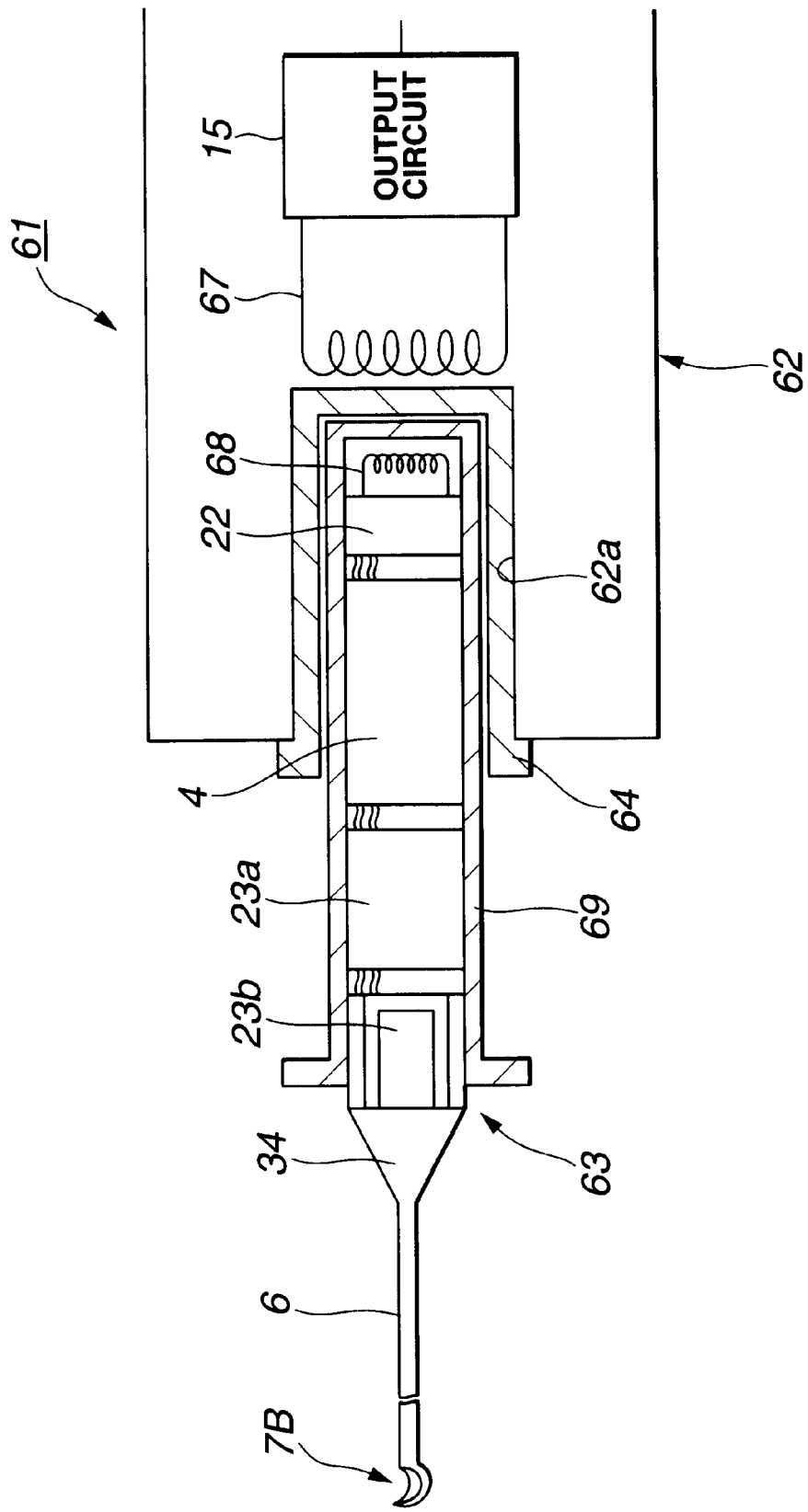

FIG. 10 shows a rechargeable ultrasonic coagulation/incision apparatus 61 comprised of a recharger 62 and an ultrasonic coagulation/incision instrument 63 having a built-in secondary battery 4 (see FIG. 11).

The recharger 62 has receptacle attachment/detachment recesses 62a (see FIG. 12) which receive recharge receptacles. The receptacles are removable for washing and sterilization.

Prior to surgery, the ultrasonic coagulation/incision instrument 63 and recharge receptacles 64 are sterilized. For use, the recharge receptacles 64 are mounted in the recharger 62, and the ultrasonic coagulation/incision instrument 63 is inserted.

As shown in FIG. 11, the recharger 62 has, for example, a primary coil 67 as the power transmission circuit 16. A secondary coil 68 (serving as the power reception unit 21) is placed inside a housing 69 of the hand-held portion 5 of the ultrasonic coagulation/incision instrument 63. Energy is propagated to the secondary coil 68 due to electromagnetic induction. The energy is converted into a voltage suitable for recharge by means of the rectification control unit 22 connected to the secondary coil 68, and then applied to the secondary battery 4. The secondary battery 4 is thus recharged.

The recharge receptacles 64 are made of a resin such as Teflon or a ceramic that is resistant to disinfection and sterilization. The recharge receptacles 64 are electrically insulated. Although each recharge receptacle 64 is interposed between the primary coil 67 and secondary coil 68, electromagnetic energy induced in the primary coil 67 can be propagated to the secondary coil 68.

The secondary battery 4 is connected to the ultrasonic generator circuit 23a via a switch (not shown). When the switch is turned on, an oscillating output of the ultrasonic generator circuit 23a is applied to the ultrasonic transducer 23b. Ultrasonic waves generated from the ultrasonic transducer 23b are propagated to the distal treatment section 7B via the horn 34 and axial portion 6, and cause the distal treatment section 7B to oscillate at an ultrasonic frequency.

According to the fourth embodiment, each recharge receptacle 64 is interposed between the primary coil 67 and secondary coil 68. Consequently, recharge can be achieved with the ultrasonic coagulation/incision instrument left sterilized.

Fifth Embodiment

Figure 13A:
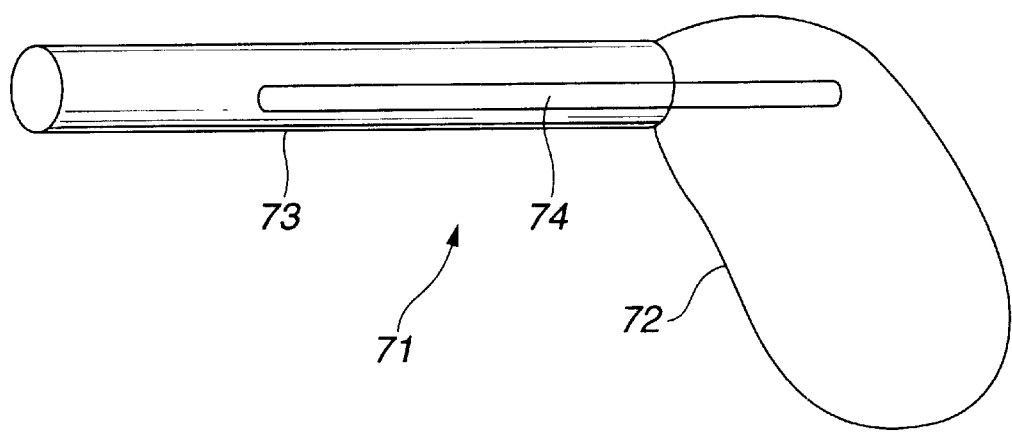
FIG. 13A and FIG. 13B schematically show a surgical instrument in accordance with the fifth embodiment of the present invention.

The fifth embodiment of the present invention will be described with reference to FIG. 13A. FIG. 13A shows a battery-driven treatment instrument 71 to be employed in endoscopic surgery. The battery-driven treatment instrument 71 is comprised of an operation unit 72 and an insertion unit 73. A secondary battery 74 extends through the operation unit 72 and insertion unit 73.

Figure 13B:
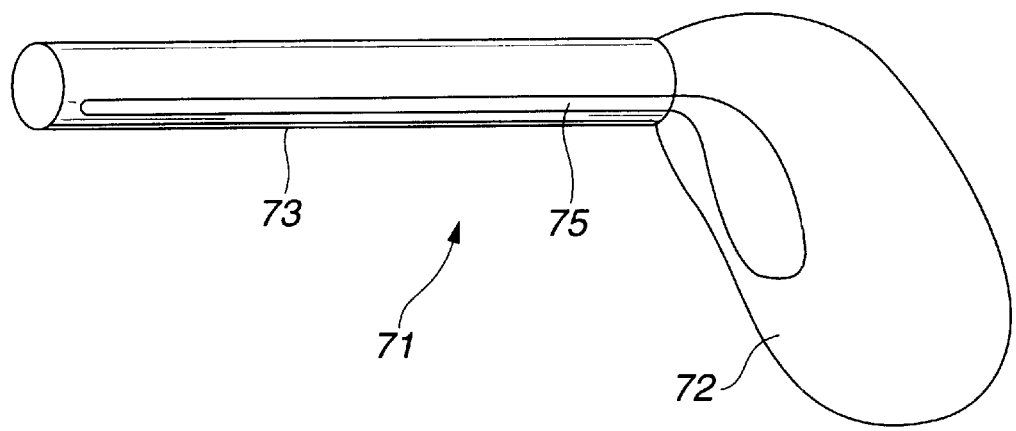

FIG. 13B shows another battery-driven treatment instrument 71' to be employed in endoscopic surgery. A differently-shaped secondary battery 75 extends through the operation unit 72 and insertion unit 73. The power reception unit 21 employed in, for example, the first embodiment is incorporated in the operation unit 72 (not shown).

An advantage of the fifth embodiment is that the relatively heavy secondary battery 74 or 75 is extends through the both insertion unit 73 and operation unit 72, the treatment instrument is well balanced and easy to use.

As mentioned previously, according to the first to fifth embodiments, a secondary battery in a surgical instrument can be recharged while held in noncontact with an energy generation unit. In other words, the secondary battery can be recharged with the sterilized surgical instrument left uncontaminated. Moreover, the necessity of renewing a battery during surgery can be substantially obviated.

In the embodiments of surgical instruments described below, it will be understood that charging units as described in connection with the first through fifth embodiments may be employed, and further description will be omitted.

Several embodiments will not be described in which treatment energy output from a treatment section can be adjusted readily and quickly, and an amount of energy output to the treatment section can be adjusted to facilitate delicate or precise treatment.

Sixth Embodiment

Figure 14:
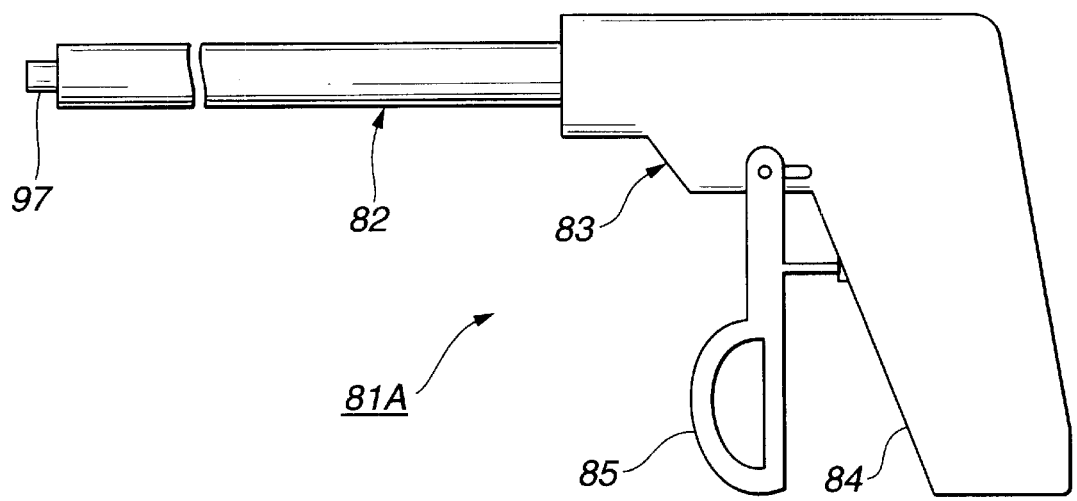
FIG. 14 to FIG. 17 relate to the sixth embodiment of the present invention.

As shown in FIG. 14, an ultrasonic treatment instrument 81A that is a motor-driven surgical instrument is comprised of an elongated insertion unit 82 to be inserted into a body cavity and an operating unit 83 formed at the back end of the insertion unit 82. The operating unit 83 is hand-held for manipulating the ultrasonic treatment instrument 81A. The operating unit 83 includes a handle portion 84 and a movable manipulation lever 85.

Figure 15:
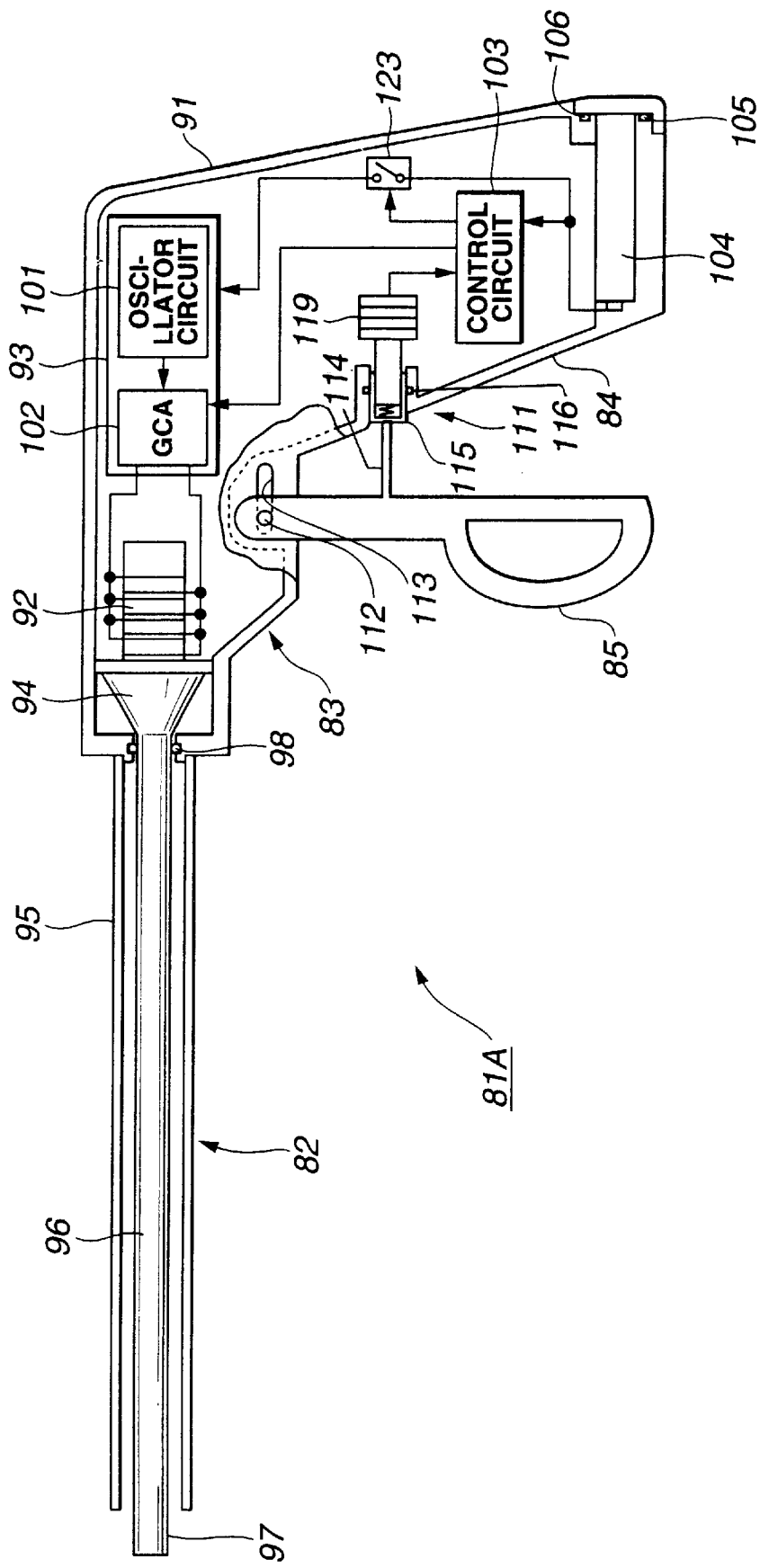

As shown in FIG. 15, the ultrasonic treatment instrument 81A has an ultrasonic transducer 82 located in a housing 91 of operating unit 83. The ultrasonic transducer 92 oscillates at an ultrasonic frequency in response to a driving signal sent from a transducer drive unit 93.

Ultrasonic waves (driving force) generated by the ultrasonic transducer 92 are propagated to an ultrasonic treatment section 97 via a horn 94 and an ultrasonic propagation rod 96. The ultrasonic propagation rod 96 is linked to the horn 94 and run through a hollow sheath 95 which forms an insertion unit. The ultrasonic treatment section 97 is formed by the distal part of the ultrasonic propagation rod 96 (extending out of the distal end of the sheath 95). The ultrasonic treatment section 97 may be in contact, for example, with a lesion. The lesion is ultrasonically heated and incised or coagulated by utilizing the ultrasonic waves.

The junction between the horn 94 and ultrasonic propagation rod 96 is sealed using a sealing O ring 98. Thus, the interior of the treatment instrument behind the horn 94 is held watertight.

The transducer drive unit 93 is comprised of an electrical oscillator circuit 101 and a gain control amplifier (GCA) 102. The gain control amplifier 102 amplifies an output of the oscillator circuit 101 at a variable amplification factor (or by a variable gain). A control circuit 103 varies the gain produced by the GCA 102. The oscillating output amplified by the gain by the GCA 102 is applied to the ultrasonic transducer 92.

The ultrasonic transducer 92 is formed, for example, by a bolted Langevin transducer having piezoelectric ceramics layered.

A battery 104 is positioned in a battery chamber in the lowermost area inside the handle portion 84.

The battery 104 supplies operating power to the control circuit 103 via a power switch (not shown). Power is supplied from the battery 104 to the transducer drive unit 93 via a switch 113.

The open end of the battery chamber is blocked with a lid 105. When the lid 105 is moved downward, the battery 104 can be replaced with a new one. A seal member such as an O ring 106 is put on the open end and abutting on the lid 105, whereby the interior of the handle portion 84 is held watertight.

According to the present embodiment, the manipulation lever 85 is movable. An output adjustment mechanism 111 cooperates with control circuit 103 to adjust ultrasonic treatment energy generated by ultrasonic treatment section 97 according to the magnitude of movement of manipulation lever 85.

Figure 16:
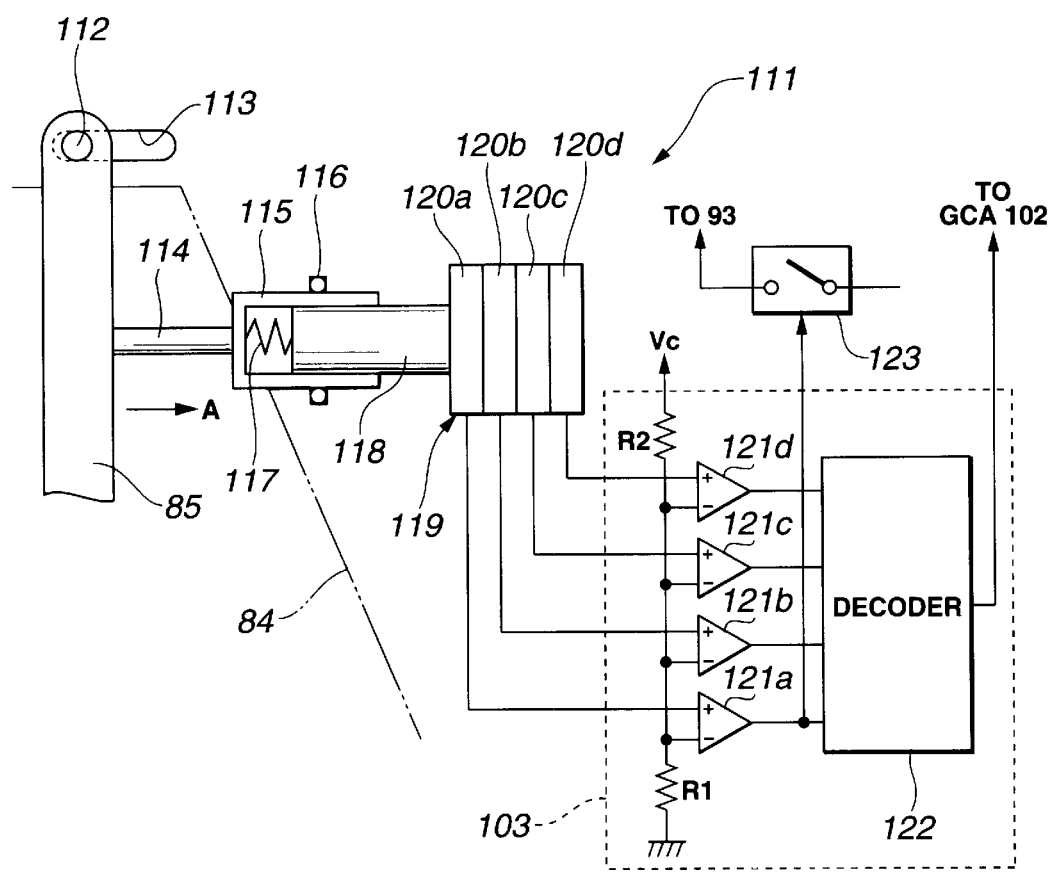

Specifically, as shown in FIG. 15 and FIG. 16, the manipulation lever 85 has a pin 112 piercing the proximal end thereof. The pin 112 is fitted in a guide groove 113 in the body of operating unit 83 and movable longitudinally therein.

As shown in FIG. 15, the portion of the housing 91 in which the guide groove 113 is bored is made thicker.

An arm 114 projects from near the center position in a longitudinal direction of the manipulation lever 85 towards the handle portion 84. The manipulation lever 85 is pulled towards the handle portion 84, e.g., by a finger put on the manipulation lever 85. This causes a cylinder 115 to move in a direction parallel to a longitudinal direction of the guide groove 113 (direction of arrow A in FIG. 16). The cylinder 115 is attached to the distal end of the arm 114 on the side of the handle portion.

The housing 91 of the handle portion 84 has a cylinder fitting hole into which the cylinder 115 is fitted. An O ring 116 on the perimeter of the cylinder fitting hole, provides a watertight seal.

A piston 118 based by a compression spring 112 extends out of cylinder 115. A piezoelectric switch 119 is attached to the extending portion of piston 118.

As shown in FIG. 16, the piezoelectric switch 119 has, for example, four piezoelectric elements 120a, 120b, 120c, and 120d layered. Voltage is developed across a piezoelectric element proportional to an applied force. The voltage is output to the control circuit 103 through electrodes, which are not shown, formed on both sides of the piezoelectric element.

Each the four piezoelectric elements 120a to 120d has a different sensitivity to applied force. For example, the piezoelectric element 120a has the highest sensitivity, and the piezoelectric element 120b has the second highest sensitivity. The piezoelectric element 120c has the third highest sensitivity, and the piezoelectric element 120d has the lowest sensitivity. When the piezoelectric switch 119 is pressed with feeble force exerted by the spring 117, even the most sensitive piezoelectric element 120a will not generate any voltage.

Outputs (voltages) from the piezoelectric elements 120a to 120d are input to four comparators 121a, 121b, 121c, and 121d in the control circuit 103, and compared with a reference voltage that has undergone voltage drops caused by, for example, resistors R1 and R2. Outputs of the four comparators 121a to 121d are input to a decoder 122. The decoder 122 decodes the four outputs, produces a gain control signal whose level is proportional to the applied force, and provides the signal to the gain control terminal of the GCA 102.

The GCA 102 amplifies an input signal by a gain proportional to the voltage level of the gain control signal applied to the gain control terminal, and outputs the resultant signal. An output signal of the oscillator circuit 101 input to the GCA 102 is amplified by a gain proportional to the voltage level of the gain control signal applied to the gain control terminal of the GCA 102, and then applied to the ultrasonic transducer 92.

The output of the comparator 121a is also used to control whether an analog switch 123 is turned on or off. The analog switch 123 is connected in series with the power switch (not shown), and interposed between the secondary battery 104 and the power terminal of the transducer drive unit 93. When the manipulation lever 85 is manipulated to the extent that the threshold force for piezoelectric element 120a is exceeded, an output from the most sensitive comparator 121a is driven high, driving power is supplied from the secondary battery 104 to the oscillator circuit 101 and GCA 102.

In other words, according to the present embodiment, when the power switch is manipulated, power is supplied from the secondary battery 104 to the control circuit 103 and analog switch 123. Power is supplied to the transducer drive unit 93 only when the manipulation lever 85 is moved to such an extent that the output from the comparator 121a assumes a certain voltage level or more. This is intended to save electrical energy to be consumed by the transducer drive unit 93 when the manipulation lever 85 remains unmoved.

Operations to be exerted by the ultrasonic treatment instrument 81A of the sixth embodiment having the foregoing components will be described below.

Assume that, for example, the ultrasonic treatment instrument is inserted into the abdominal cavity for resetting a lesion or performing surgery to arrest bleeding. In this case, an endoscope (not shown) is inserted into the abdominal cavity using a trocar and cannula so that a lesion can be observed, and the ultrasonic treatment 81A is inserted while guided with the trocar and cannula.

When it becomes possible to observe the lesion and the distal part of the ultrasonic treatment instrument 81A using the endoscope, the power switch of the ultrasonic treatment instrument 81A is turned on to actuate the control circuit 103. The distal treatment section 97 of the insertion unit 82 is abutted against the lesion. In this state, the handle portion 84 of the operation unit 83 is held with a hand, and a finger is rested on the finger rest of the manipulation lever 85. The manipulation lever 85 is then pulled towards the handle portion 84.

When the piston 118 is left pressed against the piezoelectric switch 119 due to elastic force exerted by the spring 117, pressing force is applied to the four piezoelectric elements 120a to 120d constituting the piezoelectric switch 119. The pressing force is proportional to manipulating force with which the manipulation lever 85 is pulled towards the handle portion 84.

When voltage generated by the most sensitive piezoelectric element 120a exceeds a reference level due to the pressing force, an output of the comparator 121a is driven high and the switch 123 is turned on. Consequently, power is supplied to the transducer drive unit 93.

The oscillator circuit 101 then oscillates. An oscillating output of the oscillator circuit is applied to the ultrasonic transducer 92 via the GCA 102.

Assuming that the applied force is small, when voltage generated by the piezoelectric element 120a exceeds the reference level, voltages generated by all the piezoelectric elements 120a to 120d have exceeded the reference level.

When the output of the comparator 121a alone is driven high, the gain produced by the GCA 102 is small, and the amplitude of a transducer driving signal to be applied to the ultrasonic transducer 92 is small. Consequently, the amount of ultrasonic treatment energy output from the treatment section 97 is small.

Moreover, when the outputs of all the comparators 121a to 121d are driven high, the gain produced by the GCA 102 is the largest and the amplitude of the transducer driving signal to be applied to the ultrasonic transducer 92 is the largest. Consequently, the amount of ultrasonic treatment energy output from the treatment section 97 is large.

Consequently, force with which the manipulation lever 85 is pulled towards the handle portion 84 is adjusted so that an amount of ultrasonic output energy suitable for incision can be produced.

For coagulating a bleeding lesion, the force with which the manipulation lever 85 is pulled towards the handle portion 84 is adjusted to thus set the amount of ultrasonic treatment output energy to a value proportional to the magnitude of force. Consequently, the lesion to be coagulated can be treated with the ultrasonic treatment energy output from the magnitude suitable for coagulation.

According to the present embodiment, the manipulation lever 85 is manipulated with a finger of a hand holding the operation unit 83 of the ultrasonic treatment instrument 81A. The output of the distal treatment section 97 of the insertion unit 82 can be readily varied nearly proportionally to the manipulating force. An operator can therefore readily set the amount of treatment output energy to his/her desired value.

Moreover, since an amount of energy can be varied with a simple manipulation performed with a hand holding the ultrasonic treatment instrument, a surgical procedure requiring a precise and delicate skill can be carried out smoothly.

Figure 17:
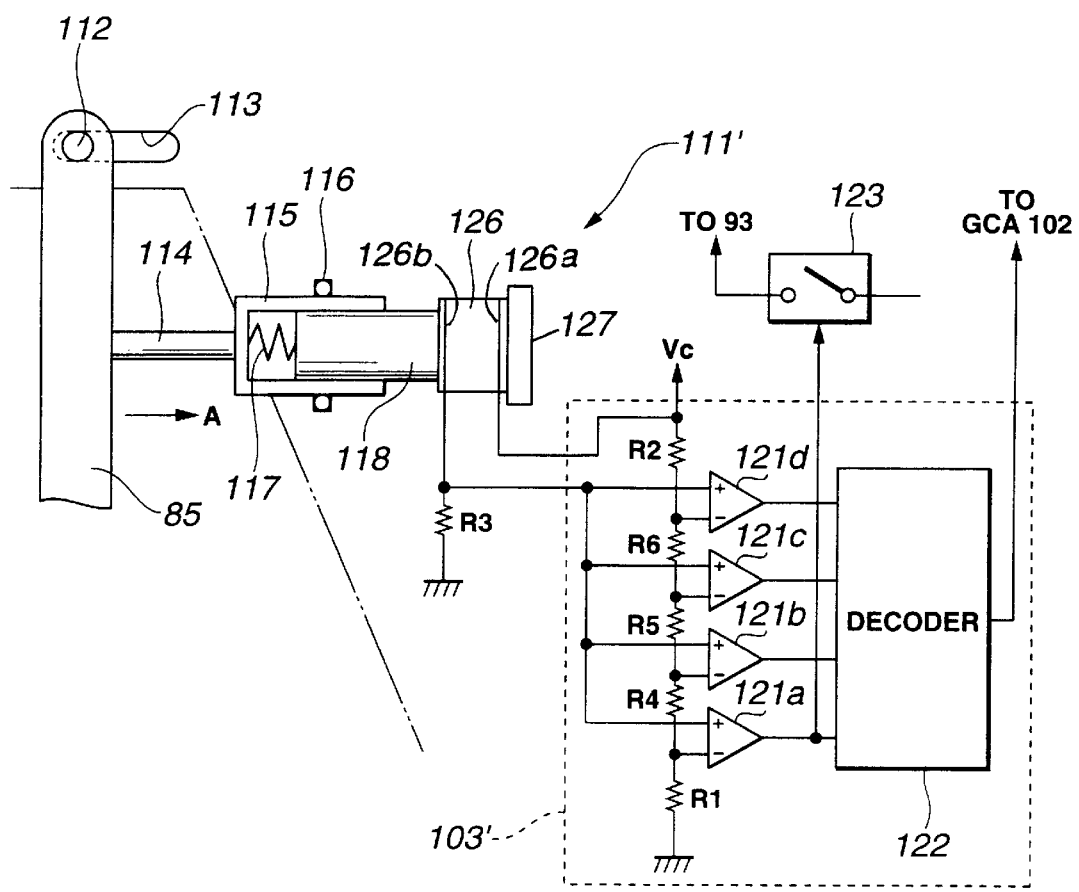

FIG. 17 shows an alternative output adjustment mechanism 111'. In this variant, an elastic-conducting device 126 having conductivity and elasticity is used instead of the piezoelectric switch 119 shown in FIG. 16. When the elastic-conducting device 126 is compressed, its resistance decreases.

The elastic-conducting device 126 has one end thereof fixed to a restriction plate 127 positioned in the housing and the other end abutted on piston 118 biased by spring 117.

One of the electrodes 126a formed on elastic-conducting device 126 is connected to a power terminal Vc (the positive electrode of the secondary battery 104), and the other electrode 126b is connected to a ground terminal via a resistor R3. Electrode 126b is also connected to the noninverting output terminals of the comparators 121a, 121b, 121c, and 121d comprising a control circuit 103'.

The inverting output terminal of the comparator 121a shown in FIG. 16 is grounded via a resistor R1, and the inverting input terminal of comparator 121d is connected to the power terminal via a resistor R2.

In the variant shown in FIG. 17, resistors R4, R5, and R6 are connected, respectively, between the inverting input terminals of the comparators 121a and 121b, 121b and 121c, and 121c and 121d. Resistors R4–R6 are also connected in series with resistors R1 and R2 between the battery and ground.

The other components are identical to those of the sixth embodiment. Accordingly, in the variant of FIG. 17, when manipulation lever 85 is pressed, the piston 118 exerts force, elastic-conducting device 126, and the resistance thereof is reduced. Voltage to be applied to the noninverting output terminals of the comparators 121a to 121a increases accordingly.

When the voltage exceeds a reference level determined with voltage applied to the noninverting input terminal of the comparator 121a, the switch 123 is turned on. The outputs of the comparators 121a to 121d are decoded by the decoder 122. A gain control signal proportional to force with which the elastic-conducting device 126 experience is thus applied to the GCA 102. The amplitude of a driving signal used to drive the ultrasonic transducer 92 is thus controlled.

Moreover, an amount of treatment energy output from the treatment section 97 is set to a value proportional to the amplitude of the driving signal. In short, this variant provides substantially the same operations and advantages as the sixth embodiment. In addition, however, it is observed that with a piezoelectric switch, voltages generated by the piezoelectric elements 120a to 120d are likely to be neutralized due to movement of charges made during a specific time interval. For this reason, if the manipulating force applied to lever 85 changes slowly, the generated voltages tend to decrease. This variant of FIG. 17 is not susceptible to this phenomenon.

Seventh Embodiment

Figure 18:
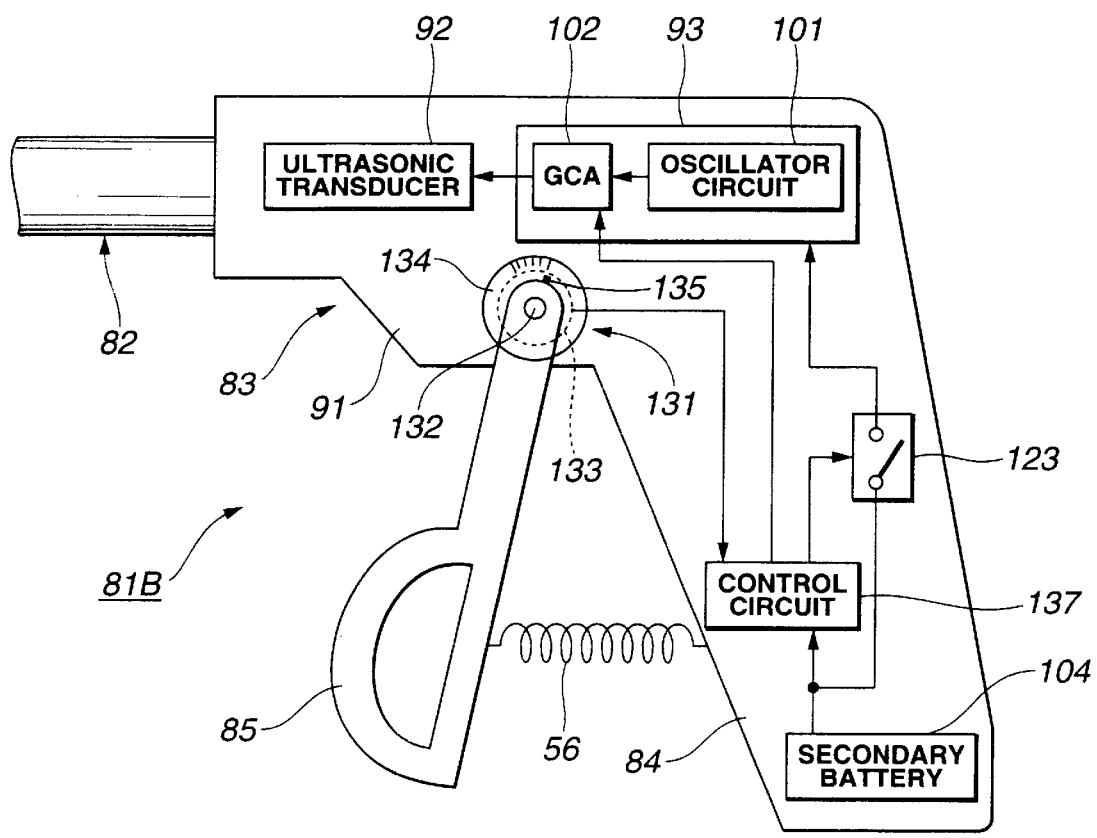
FIG. 18 shows the configuration of an output adjustment mechanism and others included in an ultrasonic treatment instrument in accordance with the seventh embodiment of the present invention.

An ultrasonic treatment instrument 81B in accordance with the seventh embodiment shown in FIG. 18 has an output adjustment mechanism 131 partly different from the output adjustment mechanism 111 employed in the sixth embodiment.

An axis 132 piercing the proximal end of the manipulation lever 85 is fitted in a hole bored in the housing 91 and thus rotationally supported. An angle detection device 133 realized with, for example, a potentiometer is attached to the end of the axis 132 projecting into the housing 91.

When the manipulation lever 85 is turned, the potentiometer serving as the angle detection device 133 and coupled to the axis 132 is rotated. Resistance varies proportionally to the angle of rotation.

Moreover, a scale plate 134 is attached on the perimeter of the axis 132 piercing the proximal end of the manipulation lever 85. A pointer 135 is attached to lever 85. An angle of rotation by which the axis 132 is rotated by moving the manipulation lever 85 is may be thus read from the scale plate using pointer 135.

A spring 136 is interposed between the manipulation lever 85 and handle portion 84. The spring 136 constrains the manipulation lever 85 to open. The angle detection device 133 outputs a resistance value or a voltage value, which is proportional to the angle of rotation by which the manipulation lever 85 is turned, to a control circuit 137.

The control circuit 137 sends a signal, of which level is proportional to an output value of the angle detection device 133, to the GCA 102 in the transducer drive unit 93. The control circuit 137 includes the comparator 121a shown in FIG. 16. When the manipulation lever 85 is turned a little towards the handle portion 84, if the output value of the angle detection device 133 exceeds a small reference value, power to be supplied to the transducer drive unit 93 is controlled by turning on or off the switch 123.

The secondary battery 104 supplies operating power to the control circuit 137 and to the transducer drive unit 93 via the switch 123.

The other components are identical to those of the sixth embodiment.

The present embodiment exerts the same operations as the sixth embodiment. Specifically, when the manipulation lever 85 is manipulated, the axis 132 is rotated by an angle substantially proportional to the magnitude of manipulating force. When the angle of rotation exceeds a reference value, the control circuit 137 turns on the switch 123 so that power will be supplied to the transducer drive unit 93. The control circuit 137 outputs a gain control signal, of which level is proportional to the angle of rotation, to the GCA 102, and thus controls the amplitude of a driving signal, which is used to drive the ultrasonic transducer 92, proportionally to the angle of rotation.

Consequently, an amount of treatment energy output from the treatment section 97 is set to a value nearly proportional to the magnitude of manipulating force with which the manipulation lever 85 is manipulated.

According to the present embodiment, the manipulation lever 85 is manipulated with a finger of a hand holding the operating unit 83 of the ultrasonic treatment instrument 81. An output from the distal treatment section 97 of the insertion unit 82 can be readily varied nearly proportionally to the manipulating force. Consequently, an operator can readily set the amount of treatment output energy to his/her desired value, and can quickly perform treatment for cure.

Moreover, the amount of treatment output energy can be varied using a hand holding the operating unit. This is helpful in performing a delicate surgical procedure for precise treatment.

Moreover, according to the present embodiment, an angle of rotation or a magnitude of manipulating force with which the manipulation lever 85 is manipulated can be discerned from the reading of the scale plate 134. The amount of treatment energy output from the treatment section 97 can be checked based on the angle of rotation or the magnitude of manipulating force. In short, according to the present embodiment, the variable amount of treatment output energy can be checked from the reading of the scale plate 134 pointed out by the jut 135.

Even in the sixth embodiment, a scale may be formed in a longitudinal direction of the guide groove 113 so that the position within the guide groove 113 at which the pin 112 piercing the proximal end of the manipulation lever 85 is located can be discerned.

Moreover, the present invention is not limited to the means for discerning the amount of treatment output energy using the scale plate 134. Alternatively, an indicator formed with an LED or the like maybe used to electrically indicate the amount of treatment output energy. Otherwise, the value of an output (voltage, current, or power) actually applied to the ultrasonic transducer 92 may be electrically indicated.

Eighth Embodiment

Next, the eighth embodiment of the present invention will be described with reference to FIG. 19 and FIG. 20. A high-frequency treatment instrument in accordance with the present embodiment is different from that of the sixth embodiment in terms of an output adjustment mechanism.

Figure 19:
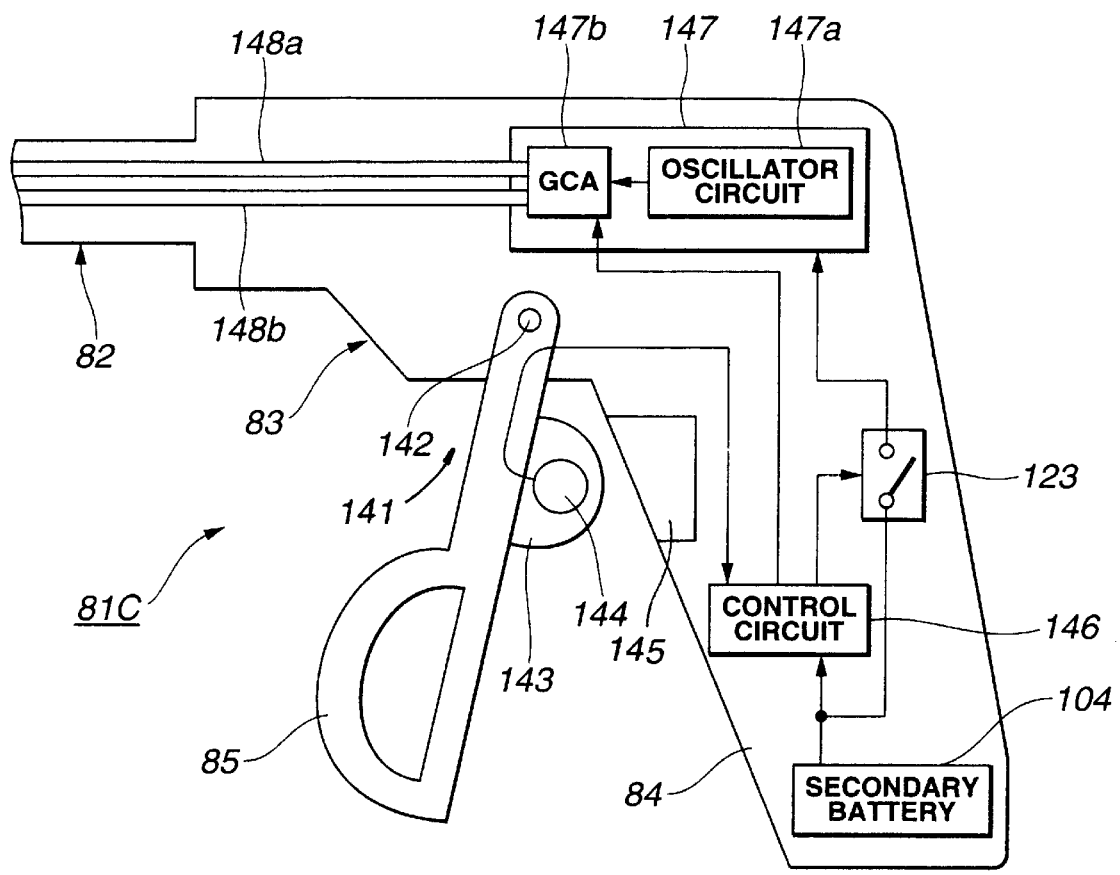
FIG. 19 and FIG. 20 relate to the eighth embodiment of the present invention.

A high-frequency treatment instrument 81C shown in FIG. 19 has an output adjustment mechanism 141. The manipulation lever 85 has the proximal end thereof journaled so that the manipulation lever can pivot freely with an axis of rotation 142 as a center. A hemisphere projection 143 is formed near the proximal end of the manipulation lever 85, and a strain detection device 144 is embedded in the projection. An elastic rubber insert 145 having elasticity is located at a position in the handle portion 84 at which it is opposed to the projection 143. The projection 143 is formed with an elastic member whose hardness is higher than that of the insert 145. Force applied to the projection 143 is conveyed to the strain detection device 144.

When lever 85 is manipulated, the projection 143 abuts against insert 145 and presses it. An output proportional to the pressing force is then provided by the strain detection device 144 to a control circuit 146. When the projection 143 hits insert 145, it is deformed by projection 143. This permits the lever 85 to pivot with the axis of rotation 142 as a center.

When a signal from the strain detection device 144 exceeds a reference level, the control circuit 146 turns on the switch 123. Also, the control circuit 146 controls a high-frequency treatment instrument drive unit 147 according to an output signal proportional to the signal input from the strain detection device 144.

The high-frequency treatment instrument drive unit 147 consists of, for example, an oscillator 147a and a GCA 147b for amplifying an oscillating output of the oscillator 147a. The control circuit 146 varies a gain, which is produced by the GCA 147b, proportionally to the signal input from the strain detection device 144, and thus varies an amount of high-frequency treatment energy provided by distal treatment section via electrodes 148a and 148b connected to the GCA 147b.

Figure 20:
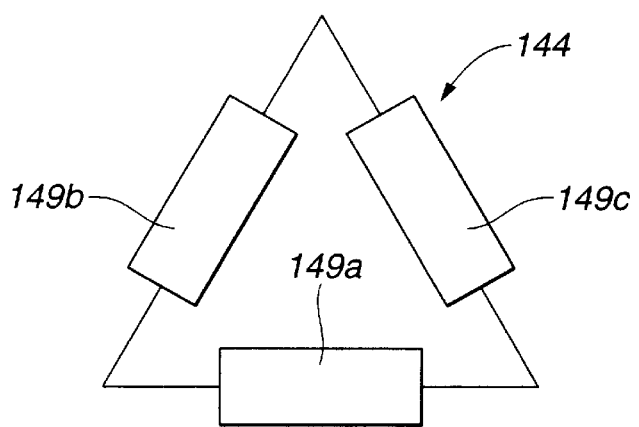

FIG. 20 shows the details of the strain detection device 144. The strain detection device 144 consists of, for example, three strain gages 149a, 149b, and 149c which constitute a bridge. The strain detection device 144 outputs a signal, which represents a magnitude of strain proportional to the magnitude of pressing force with which the manipulation lever 85 is pressed, to the control circuit 146.

The other components are identical to those of the sixth embodiment.

According to the present embodiment, high-frequency power generated by the high-frequency treatment instrument drive unit 147 is propagated to the distal treatment section over the electrodes 148a and 148b. The treatment section is used to perform treatment such as cautery using high-frequency energy.

Even in the present embodiment, an amount of treatment output energy with which high-frequency treatment is carried out can be varied. The treatment output energy is generated by the high-frequency treatment instrument drive unit 147 according to the manipulating force with which the manipulation lever 85 is turned, and then propagated to the treatment section over the electrodes 148a and 148b.

The present embodiment has substantially the same advantages as the sixth embodiment or its variant.

According to a variant of the present embodiment, strain detection device 144 may be embedded in the elastic rubber insert 145. In this variant, an output signal of the strain detection device 144 can readily be provided to the control circuit 146 without need for a signal line laid down in the manipulation lever 85 that is movable. This results in a simpler configuration.

Ninth Embodiment

Next, the ninth embodiment of the present invention will be described with reference to FIG. 21 and FIG. 22.

Figure 21:
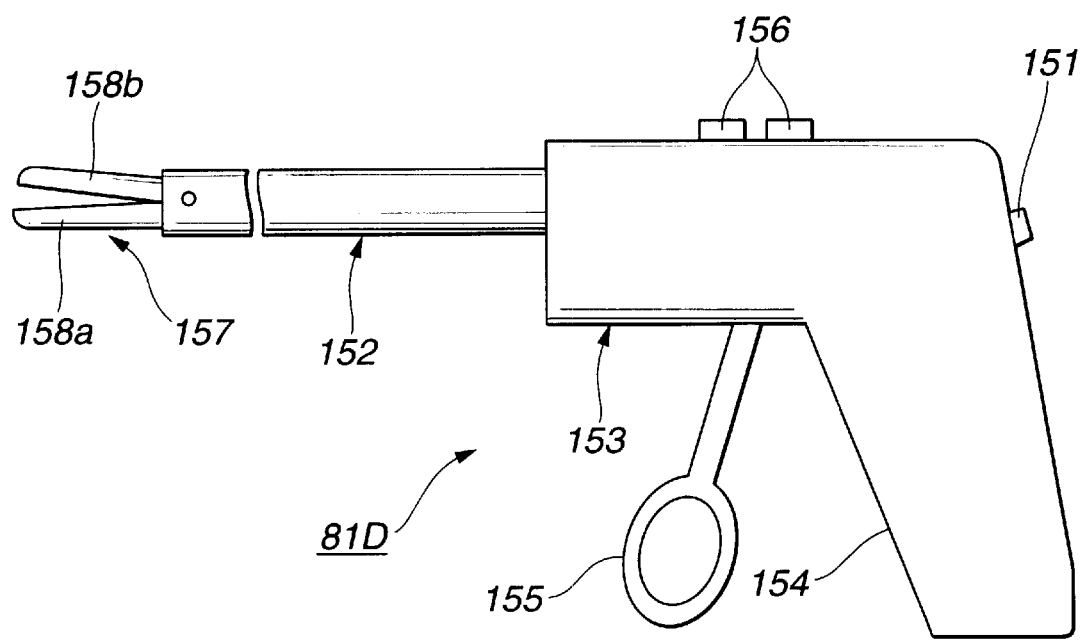
FIG. 21 and FIG. 22 relate to the fourth embodiment of the present invention.

As shown in FIG. 21, an ultrasonic treatment instrument 81D consists mainly of an insertion unit 152 and an operating unit 153. The operating unit 153 has a handle portion 154 and a manipulation lever 155. On and Off switches 156 are formed on the top of the operation unit 153. An output adjustment switch 151 made of a conducting rubber is located at an upper position on the handle portion 154.

The output adjustment switch 151 has basically the same structure as the elastic-conducting device 126 shown in FIG. 17. When the elastic-conducting device 126 is pressed, its electrical resistance varies depends on pressure applied by the thumb of the user. A control circuit 168 (see FIG. 22) detects the resistance in the form of a voltage drop, and varies the amplitude of a transducer driving signal output from the transducer drive unit 93.

According to the present embodiment, a distal treatment section 157 of the insertion unit 152 consists of a stationary jaw 158a and a movable jaw 158b. The movable jaw 158b is coupled to a pulley 161 (see FIG. 22) by way of an operating wire 159 (see FIG. 22) passed through the insertion unit 152. The pulley 161 is located near the proximal end of the manipulation lever 155. When the manipulation lever 155 is turned, the movable jaw 158b pivots with a pin piercing the proximal end thereof as a center. The movable jaw 158b thus opens or closes relative to the stationary jaw 158a.

Figure 22:
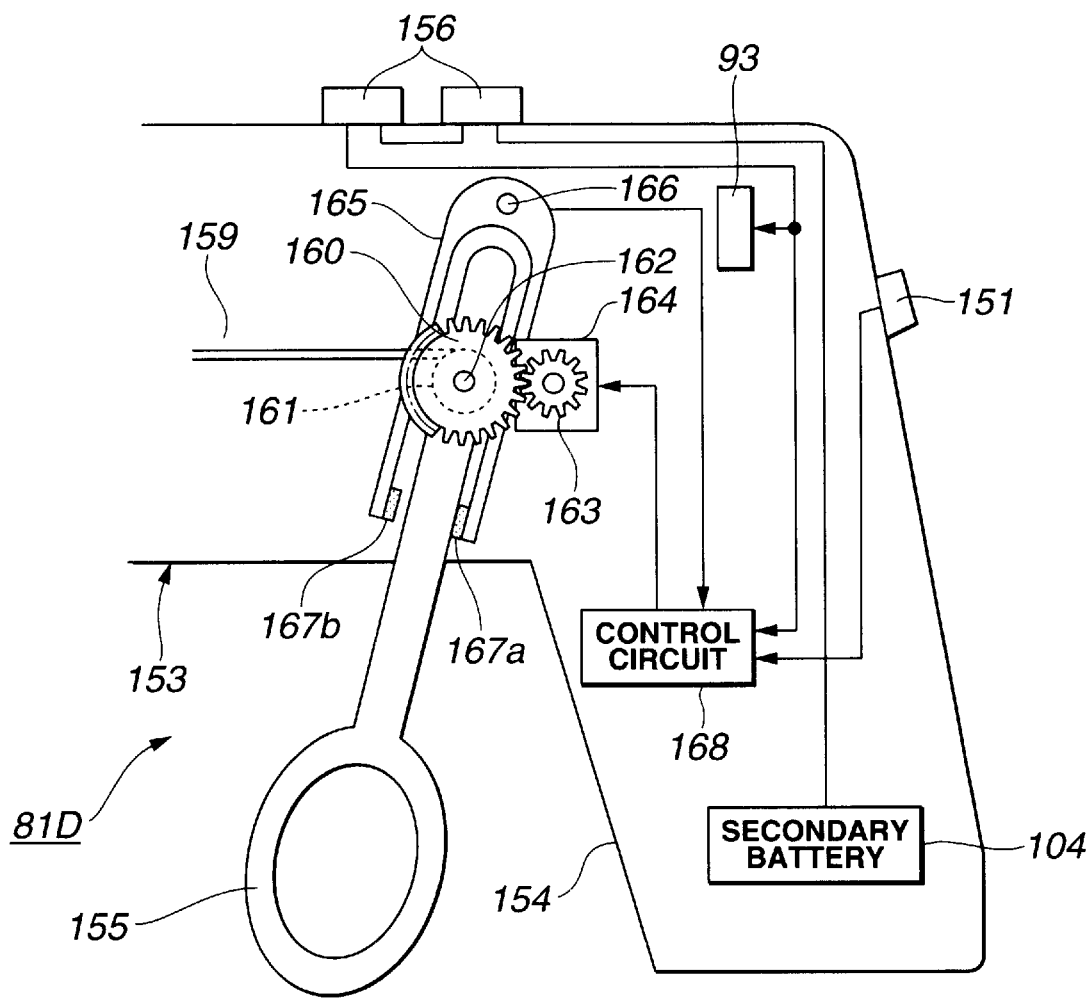

FIG. 22 shows the details of the manipulation lever 155 and handle portion 154. A gear 160 and the pulley 161 are located near the proximal end of the manipulation lever 154 so that they can rotate freely with respect to an axis of rotation 162. The gear 160 is connected to a motor 164 via a gear 163 engaged with the gear 160. The motor 164 is attached to the axis of rotation of the gear 163. The gear 163 rotates along with rotation of the motor 164.

Moreover, the back end of the operation wire 159 is linked to the pulley 161 freely rotational together with the gear 160. When the pulley 161 is rotated, the movable jaw 158b opens or closes relative to the stationary jaw 158a.

A pressure sensor fixture 165 is formed to surround the proximal part of the manipulation lever 154. The pressure sensor fixture 165 is shaped substantially like letter U, and journaled in, as shown in FIG. 22, an axis of rotation 166 at the upper end of the pressure sensor fixture. Pressure sensors 167a and 167b sensitive to pressure are attached to the ends of fork portions of the pressure sensor fixture 165. The pressure sensors 167a and 167b can come into contact with the side edges of the manipulation lever 155.

The secondary battery 104 supplies power to a control circuit 168 and the transducer drive unit 93 via the On and Off switches 156.

Outputs of the pressure sensors 167a and 167b are input to the control circuit 168 and used to control rotation of the motor 164.

To be more specific, when the pressure sensors 167a and 167b sense pressure, the pressure-sensitive outputs of the pressure sensors are input to the control circuit 168. The control circuit 168 drives and rotates the motor 164 as long as pressure-sensitive outputs are provided. When pressure is not sensed any longer, the control circuit 168 stops driving and rotating the motor 164.

In short, once the manipulation lever 155 is manipulated, the manipulation lever 155 is electrically driven using the motor 164. Thus, the manipulation lever 155 can be moved with small force. Eventually, the movable jaw 158b can be opened or closed relative to the stationary jaw 158a.

The control circuit 168 inputs a signal stemming from a manipulation performed on the output adjustment switch 151, and thus controls the transducer drive unit 93 (gain to be produced by the GCA 102) according to the manipulating force applied to the output adjustment switch 151. Assume that power is supplied to the control circuit 168 or the like using the switch 156. When the manipulation lever 155 is moved slightly in a direction permitting the movable jaw to close (counterclockwise in FIG. 22), the side edge of the manipulation lever 155 presses the pressure sensor 167a. The pressure sensor 167a senses the pressure and supplies an output to the control circuit 168. The control circuit 168 then drives the motor 164 to help turn the manipulation lever 155 in the close direction via the gears 163 and 160. The operation wire 159 is thrust forward, whereby the distal movable jaw 158b is driven to close.

If the manipulation lever 155 is moved in the open direction permitting the movable jaw to open (clockwise in FIG. 22), the side edge of the manipulation lever 155 presses the pressure sensor 167b. The pressure sensor 167 senses the pressure and supplies an output to the control circuit 168. The control circuit 168 in turn drives the motor 164 to thus help turn the manipulation lever 155 in the open direction via the gears 163 and 160. Moreover, the operation wire 159 is wound about the pulley 161 and thus pulled backward, whereby the distal movable jaw 158b is driven to open.

When the output adjustment switch 151 is manipulated, a signal whose level is proportional to a magnitude of pressing force with which the output adjustment switch 151 is pressed is input to the control circuit 168. The control circuit 168 controls the transducer drive unit 93 (a gain to be produced by the GCA 102) according to the magnitude of pressing force.

In the present embodiment, the manipulation lever 155 can be manipulated in the open or close direction with small force. Moreover, the movable jaw 158b of the distal treatment section 157 of the insertion unit 152 can be opened or closed with small force.

To stop driving the motor 164, the manipulation lever 155 is moved to an intermediate position at which it contacts neither the pressure sensor 158a nor the pressure sensor 158b.

Moreover, the output adjustment switch 151 may be used to vary an amount of ultrasonic treatment energy output from the treatment section 157. Thus, the present embodiment has the same advantages as the sixth embodiment.

Tenth Embodiment

Next, the tenth embodiment of the present invention will be described with reference to FIG. 23. The tenth embodiment is identical to the ninth embodiment except that the movable jaw 158b is normally open and can be closed with a small manipulating force.

Figure 23:
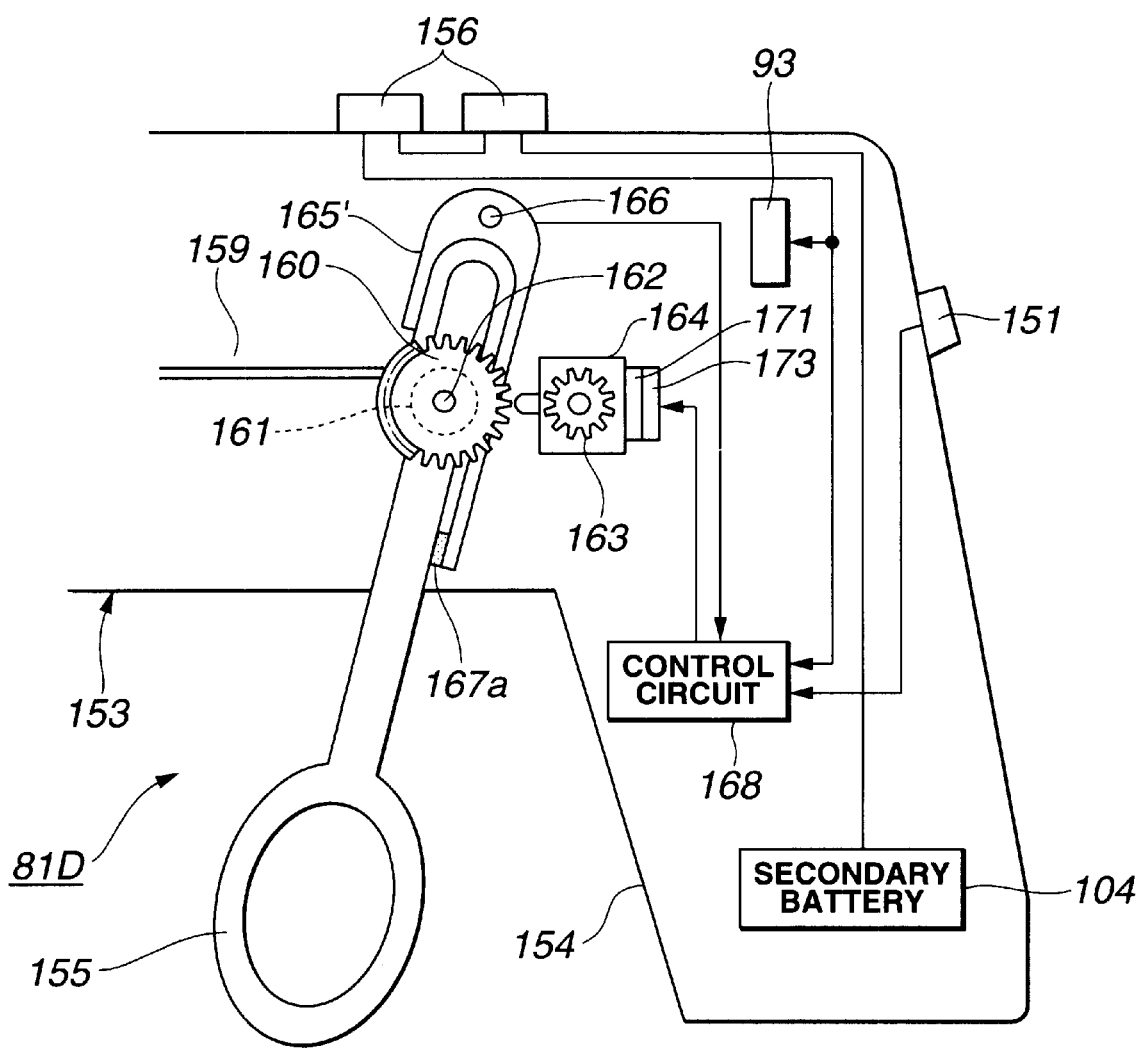
FIG. 23 shows the configuration of the major portion of an ultrasonic treatment instrument in accordance with the tenth embodiment of the present invention.

Ultrasonic treatment instrument 81E shown in FIG. 23 is comprised of a pressure sensor fixture 165' shaped like letter J, and magnet 171 is attached to the motor 164 having the gear 163. The shaft of the motor 164 (on the side of the motor opposite to the side thereof on which the gear 163 is located) is fitted in a guide groove 172 so that the shaft can be freely moved in horizontal directions.

An electromagnet 173 is placed on the magnet 171. The electromagnet 173 is connected to the control circuit 168. When current is supplied to the electromagnet 173 under the control of the control circuit 168, magnetic force repulsing the magnet 171 is generated. Consequently, the motor 164 and gear 163 can be moved towards the gear 160 along the guide groove 172.

As long as no current is supplied to the electromagnet 173, the magnet 171 is, as shown in FIG. 23, attracted to the electromagnet 173. In this state, the gear 163 is separated from the gear 160.

The other components are identical to those of the ninth embodiment shown in FIG. 22.

When the manipulation lever 155 is moved a little in the close direction, the side edge of the manipulation lever 155 presses on pressure sensor 167a. An output of the pressure sensor 167a is input to the control circuit 168. Electricity is conducted to the electromagnet 173. The resultant repulsion force causes the magnet 171 and motor 164 to move along the guide groove 172 towards the gear 160. Consequently, the gears 163 and 160 are meshed with each other. The gears 163 and 160 are rotated due to the motor 164, whereby the manipulation lever 155 is turned in the close direction.

When the side edge of the manipulation lever 155 does not press the pressure sensor 167a, the pressure sensor 167a does not produce an output signal. Accordingly, the control circuit 168 that receives an output of the pressure sensor 167a stops supplying current to the electromagnet 173. The magnet 171 is therefore attracted to the electromagnet 173. The gears 160 and 163 are separated from each other and the motor 164 stops rotating.

Moreover, when the output adjustment switch 151 is manipulated, a signal whose level is proportional to the magnitude of the manipulating force with which the output adjustment switch 151 is pressed is input to the control circuit 168. The control circuit 168 in turn controls the transducer drive unit 93 (a gain to be produced by the GCA 102) according to the magnitude of pressing force.

According to the present embodiment, almost the same advantage as that of the ninth embodiment is provided when the manipulation lever is moved in the close direction.

Eleventh Embodiment

Next, the eleventh embodiment of the present invention will be described with reference to FIG. 24. This embodiment has, in addition to the same components as the ninth embodiment, a limiter means for detecting a manipulation zone in which the manipulation lever 155 can be manipulated. When the limiter means detects that the manipulation lever 155 has been manipulated beyond the manipulation zone, the motor 164 is stopped driving the manipulation lever.

Figure 24:
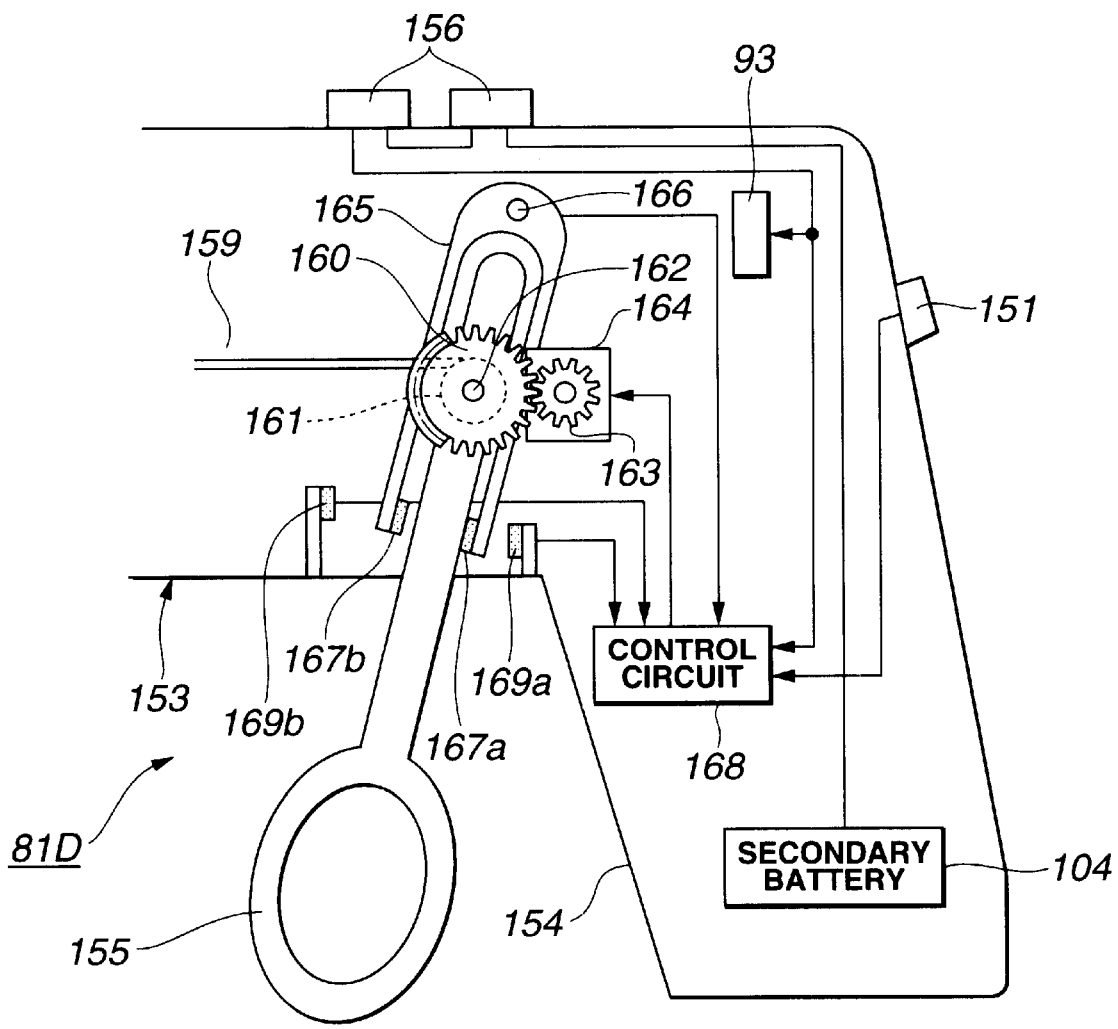
FIG. 24 shows the configuration of the major portion of an ultrasonic treatment instrument in accordance with the eleventh embodiment of the present invention.

In other words, the ultrasonic treatment instrument 81F shown in FIG. 24 is different from the ultrasonic treatment instrument 81D shown in FIG. 22 in that limit switches 169a and 169b for detecting the limits of the manipulation zone are located outside the pressure sensors 167a and 167b respectively.

Output signals of the limit switches 169a and 169b are input to the control circuit 168. In response to the signal outputs from the limit switches 169a and 169b, the control circuit 168 gives control to stop rotation of the motor 164.

Specifically, a space between the limit switches 169a and 169b provides a movable zone within which the manipulation lever 155 is movable. As long as the manipulation lever 155 is manipulated within the movable zone, the control circuit 168 gives the same control as that mentioned in conjunction with FIG. 22. When lever 155 is moved beyond the movable zone, the control circuit 168 stops rotation of the motor 164.

The other components are identical to those of the ultrasonic treatment instrument 81D shown in FIG. 22.

If the manipulation lever 155 is moved slightly in the close direction, the side edge of the manipulation lever 155 presses on pressure sensor 167a. An output of the pressure sensor 167a is then input to the control circuit 168. The control circuit 168 in turn drives the motor 164 to help turn the manipulation lever in the close direction via the gears 163 and 160.

When the manipulation lever is moved in the open direction opposite to the close direction, the side edge of the manipulation lever 155 presses the pressure sensor 167b. An output of the pressure sensor 167b is input to the control circuit 168. The control circuit 168 in turn drives the motor 164 to help turn the manipulation lever 155 in the close direction via the gears 163 and 160.

The limit switches 169a and 169b are located outside the pressure sensor fixture 165. When the manipulation lever 155 is moved in the close direction, the fork portion of the pressure sensor fixture 155 presses the limit switch 169a. The limit switch 169a senses the pressure and sends a signal to the control circuit 168. The control circuit 168 in turn stops rotation of the motor 164.

When the manipulation lever 155 is moved in the open direction, the fork portion of the pressure sensor fixture 165 presses the limit switch 169b. The limit switch 169b then senses the pressure and sends a signal to the control circuit 168. The control circuit 168 in turn stops rotation of the motor 164.

Moreover, when the output adjustment switch 151 is manipulated, a signal whose level is proportional to the magnitude of the force with which the output adjustment switch 151 is pressed, is provided to the control circuit 168.

The control circuit 168 in turn controls the transducer drive unit 93 (a gain to be produced by the GCA 102) according to the magnitude of the force.

According to the present embodiment, the same advantage as that of the ninth embodiment is provided when the manipulation lever 155 is moved within the movable zone. When the manipulation lever 155 is manipulated beyond the movable zone, it can be moved electrically. Thus, the manipulation lever can be prevented from being manipulated to an unnecessary extent.

Next, a description will be made of embodiments of a surgical instrument of improved maneuverability in which manipulation of an operating lever or the like turns a power switch on or off.

Twelfth Embodiment

Figure 25:
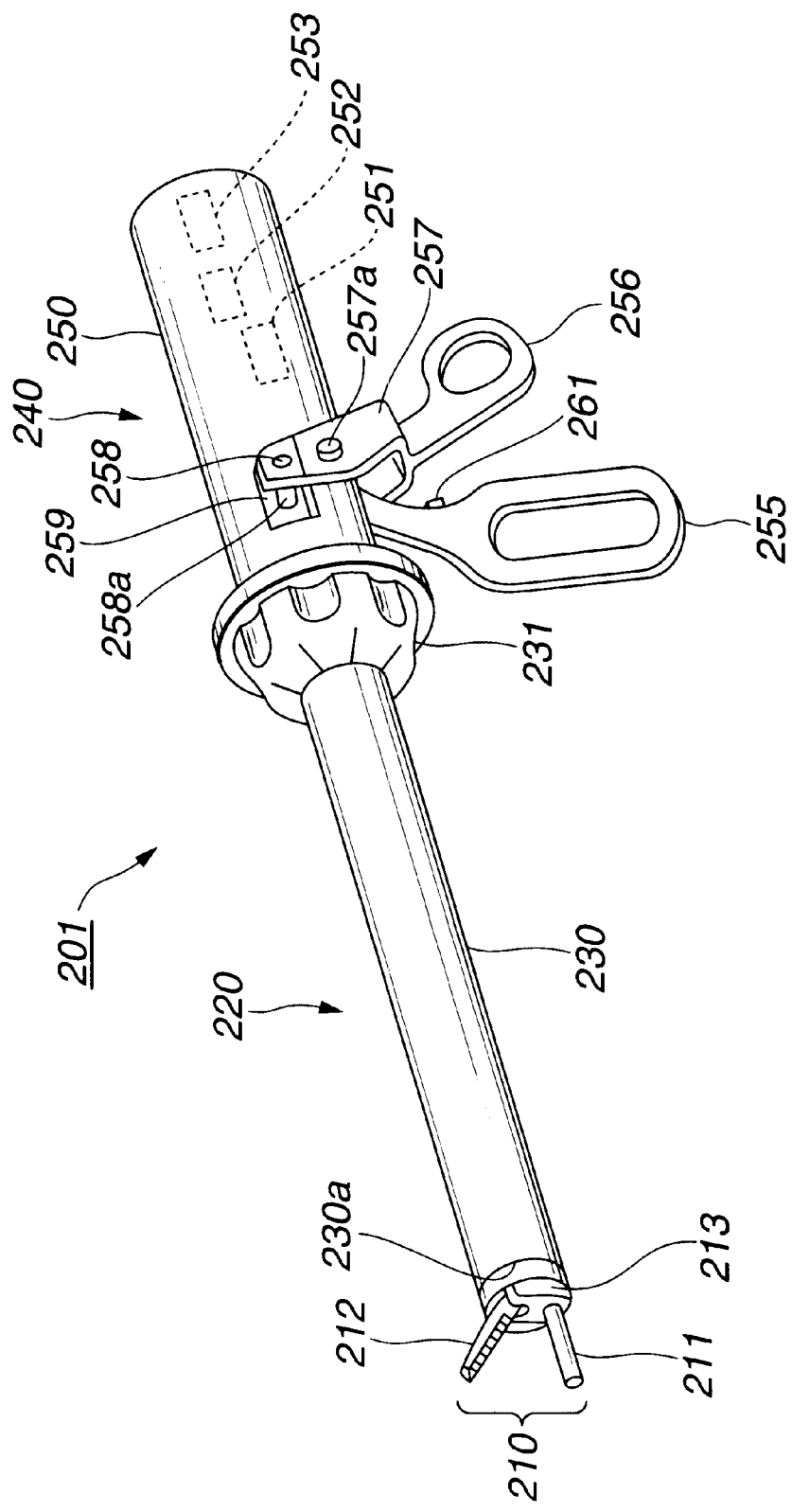
FIG. 25 to FIG. 27 relate to the twelfth embodiment of the present invention.

As shown in FIG. 25, an ultrasonic coagulation/incision instrument 201 is comprised of an insertion unit 220, a sheath 230, and a handpiece 250. The insertion unit 220 has a treatment section 210. The sheath 230 is elongated and cylindrical, and serves as a protecting member for protecting the insertion unit 220. The handpiece 250 includes a handheld operating unit 240. The proximal end of the sheath 230 is coupled to the operating unit 240 so that the proximal end can be uncoupled freely. An ultrasonic transducer 251 for generating ultrasonic waves, a drive circuit 252 for driving the ultrasonic transducer 251, and a secondary battery 253 are incorporated in the handpiece 250. The battery 253 can be renewed and serves as a power source for supplying driving power to the drive circuit 252. The ultrasonic coagulation/incision instrument 201 is a battery-powered treatment instrument having the built-in battery 253 as a driving power source.

Figure 26:
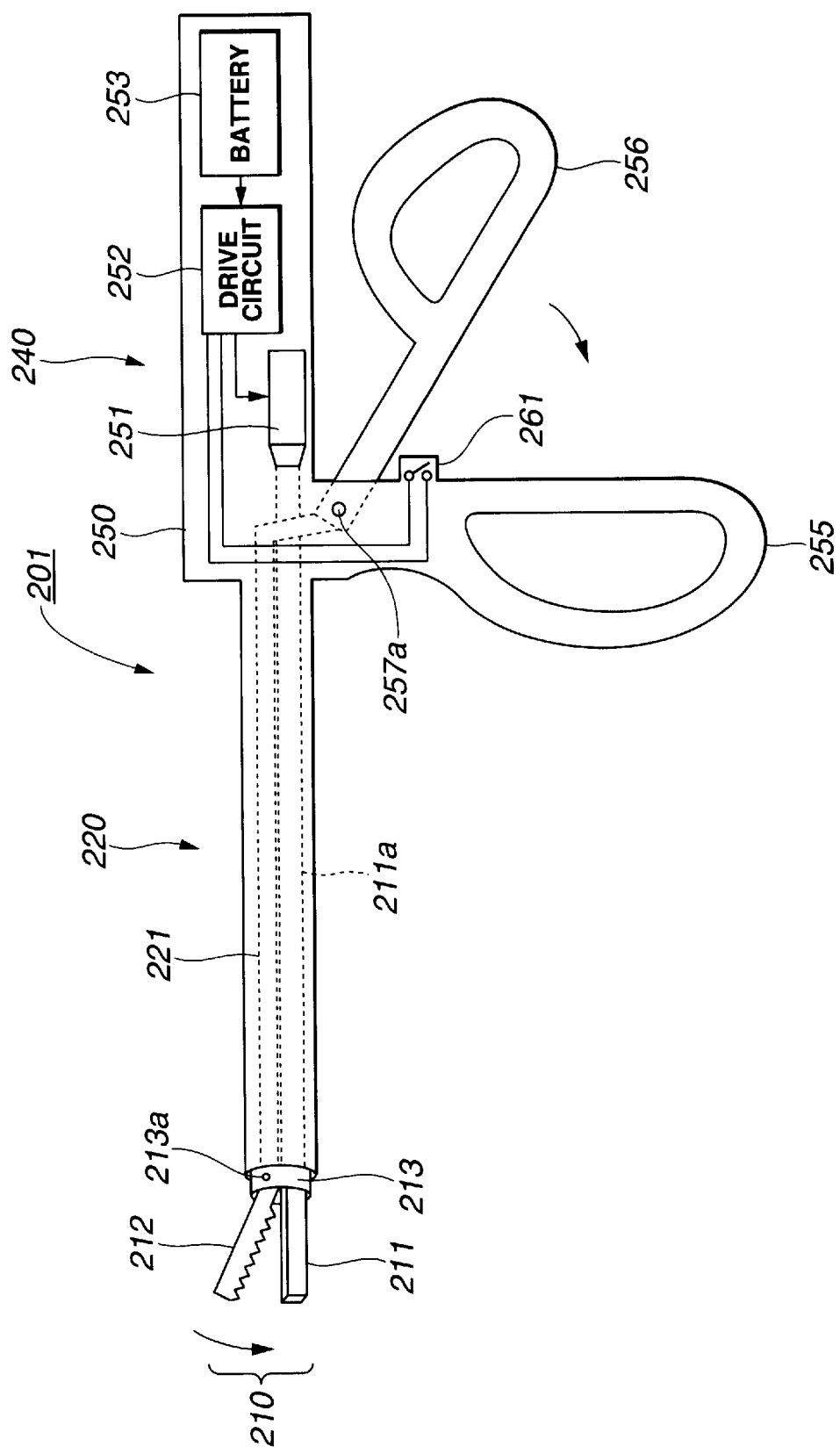

As shown in FIG. 26, ultrasonic waves generated by the ultrasonic transducer 251 in the operation unit 240 are propagated to a distal jaw 211, which is shaped like a bar, over a propagation rod 211a.

The distal treatment section 210 of the insertion unit 220 consists of the distal jaw 211 and a movable part 212 adjoining the distal jaw 211. The movable part 212 cooperates with the distal jaw 211 in clamping or freeing a living tissue. The back end of the movable part 212 is supported with a distal coupler 213 so that the movable part 212 can be opened or closed.

As shown in FIG. 25, the distal end of the sheath 230 opens as an opening 230 having a substantially oval section. The treatment section 210 of the insertion unit 220 projects from the opening 230. A rotary knob 231 is fixed as an integral part to the proximal end of the sheath 230 (end of the operating unit 240). The rotary knob 231 is used to turn the movable part 212 of the treatment section 210 with respect to the center axis of the distal jaw 211. The sheath 230 can be detached from the handpiece 250.

The operating unit 240 has an integral stationary handle 255, and a movable manipulation handle 256 movable toward or away from the stationary handle 255. A U-shaped coupling arm 257 is formed at the upper end of the movable manipulation handle 256. The substantially center position in a vertical direction on the coupling arm 257 is fixed to the operating unit 240 using a handle fulcrum pin 257a so that the coupling arm 257 can pivot freely.

A lock member 258 piercing the upper end of the coupling arm 257 is inserted towards a center-axis direction through a window 259 bored in the side of the operation unit 240. The lock member 258 has a lock claw 258a projected therefrom. The lock claw 258a locks a drive shaft 221, which will be described later, included in the insertion unit 220 within the operation unit 240 so that the drive shaft 221 can be unlocked freely (see FIG. 26).

As shown in FIG. 26, the propagation rod 211a and the drive shaft 221 are passed through the portion of the insertion unit 220 shielded with the sheath 230. The propagation rod 211a has a distal part thereof jutted out as the distal jaw 211 of the treatment section 210. The drive shaft 221 conveys a clamping or freeing motion, which is made using the movable manipulation handle 256, to the movable part 212 of the treatment section 210.

The proximal part of the propagation rod 211a is unified with the ultrasonic transducer 251 within the operation unit 240. Ultrasonic waves generated by the ultrasonic transducer 251 are propagated to the distal jaw 211 over the propagation rod. Thus, the distal jaw 211 is used to ultrasonically treat a lesion in a body cavity.

The drive shaft 221 is an operating member for conveying a clamping or releasing instruction sent from the movable manipulation handle 256 to the movable part 212. The movable part 212 is journaled in the distal end of the drive shaft 221 using a pin 213a thrust into the distal coupler 213. The back end of the drive shaft 221 is passed through the operating unit 240 and coupled to the movable manipulation handle 256.

When the movable manipulation handle 256 is moved towards the stationary handle 255, the drive shaft 221 withdraws and the movable part 212 moves towards the distal jaw 211. At this time, as the movable manipulation handle 256 is moved in order to close the movable part 212, the movable part 212 is turned to close and meet the distal part of the distal jaw 211. The movable part 212 and distal jaw 211 cooperate with each other in clamping a living tissue such as a blood vessel in a human body. In this state, when the ultrasonic transducer 251 is driven, the living tissue clamped by the distal jaw 211 and movable part 212 can be treated ultrasonically.

According to the present embodiment, a switch is formed on a side edge of the stationary handle 255. When the movable manipulation handle 256 is opened or closed relative to the stationary handle 255, the switch is turned on or off. Power is supplied from the battery 253 to the drive circuit 252 for driving the ultrasonic transducer 251 to propagate of ultrasonic waves from the ultrasonic transducer 251 to the distal jaw 211.

A driving switch 261 electrically connected to the drive circuit 252 and turned on or off by opening or closing the movable manipulation handle 256 is formed on the side edge of the stationary handle 255. Alternatively, a driving switch 261 to be turned on or off by opening or closing the movable manipulation handle 256 may be formed on the side edge of the movable manipulation handle 256.

The drive circuit 252 is electrically connected to the battery 253 and ultrasonic transducer 251. The drive circuit 252 consists mainly of an oscillator circuit (not shown) for receiving power from the battery 253 and generating a high-frequency signal, and an amplification circuit (not shown) for amplifying in power the high-frequency signal sent from the oscillator circuit and outputting a driving signal. The drive circuit 252 supplies the driving signal output from the amplification circuit to the ultrasonic transducer 251 to drive the ultrasonic transducer 251.

The distal jaw 211 and movable part 212 of the treatment section 210 are caused to clamp a living tissue by opening or closing the movable manipulation handle 256. The movable manipulation handle 256 turns on the driving switch 261 nearly at the same time. Power is then supplied from the battery 253 to the drive circuit 252, whereby the ultrasonic transducer 251 is driven. Ultrasonic waves generated by the ultrasonic transducer 251 are then propagated to the distal jaw 211, which is the distal part of the propagation rod 211a, over the propagation rod 211. Consequently, the living tissue is coagulated or incised.

When the movable manipulation handle 256 of the operation unit 240 is opened or closed, the driving switch 216 is turned on or off responsively. Treatment can therefore be performed only when needed. Besides, the maneuverability of the treatment instrument improves.

Figure 27:
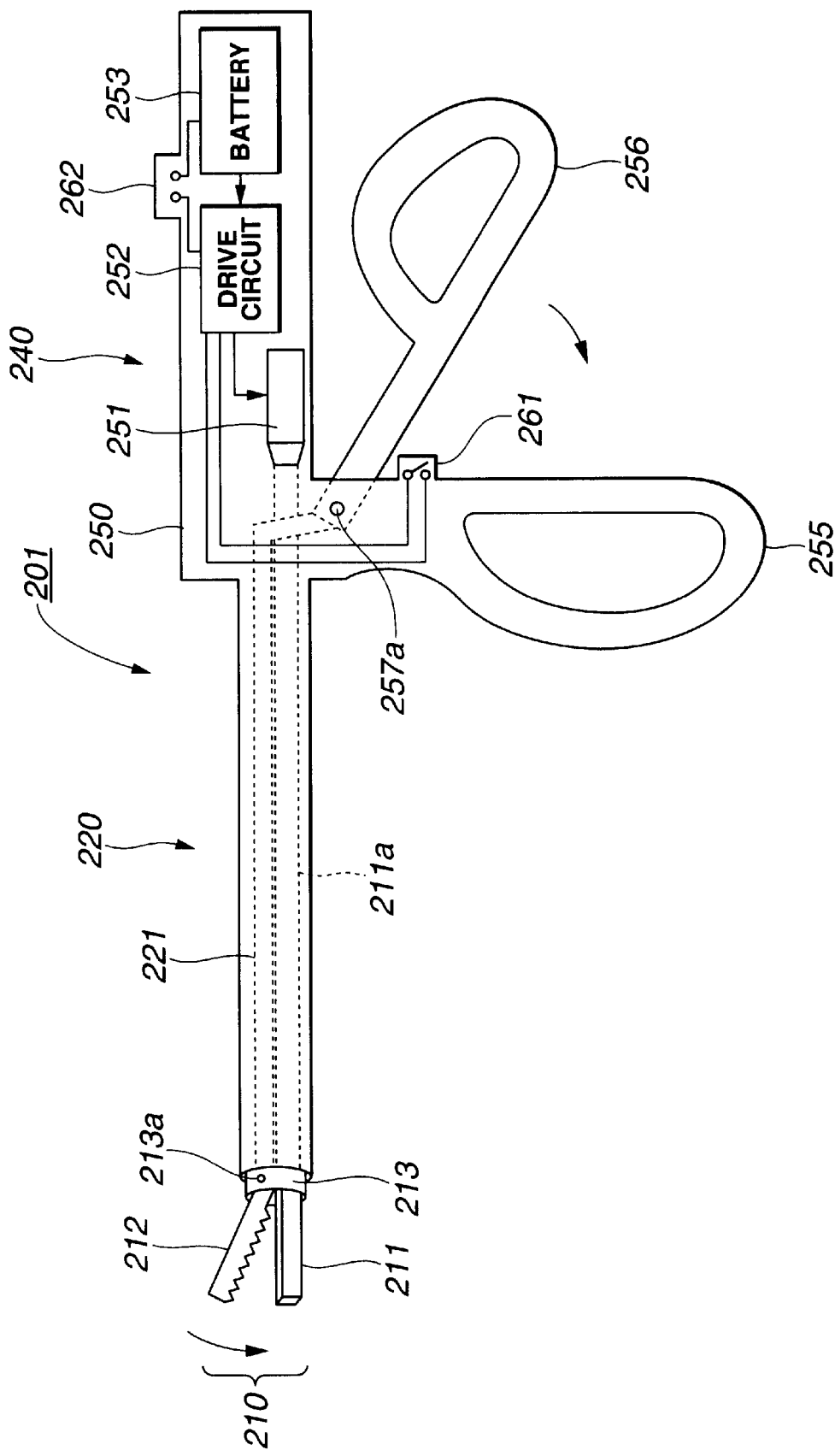

As shown in FIG. 27, in addition to the driving switch 216, a second switch 262 may be formed on the operation unit 240. After the second switch 262 is manually turned on, the movable manipulation handle 256 may be moved to turn on the driving switch 261. Thus, when a living tissue must merely be clamped with the distal jaw 211 and movable part 212, even if the movable manipulation handle 256 is opened or closed to turn on the driving switch 261, neither ultrasonic coagulation nor incision will be carried out.

The present invention will not be limited to this mode. Alternatively, a switch may be formed on an operating unit of an electric cautery or the like for exerting the operation of incision or coagulation for a living tissue using high-frequency heat energy. The operating unit may be manipulated in order to turn on or off the switch.

Moreover, according to the present embodiment, the treatment instrument is of a battery-powered type that uses a battery as a driving power source to perform various kinds of treatment on a living tissue. The present invention is not limited to this type of treatment instrument. The present invention can also be applied to a treatment instrument in which driving power or a driving signal or the like used to drive the ultrasonic transducer 251 may be supplied from an external main unit in order to carry out various kinds of treatment. In this case, after a switch formed on, for example, the external main unit is turned on, the movable manipulation handle 256 may be opened or closed to thus turn on or off the driving switch 261.

Thirteenth Embodiment

Next, the thirteenth embodiment of the present invention will be described with reference to FIG. 28.

According to the twelfth embodiment, one battery 253 is used as a driving power source for supplying driving power to an ultrasonic coagulation/incision instrument. Power supply from the battery 253 to the drive circuit 252 for driving the ultrasonic transducer 251 is controlled in order to supply ultrasonic waves from the ultrasonic transducer 251 to the distal jaw 211. In contrast, according to the thirteenth embodiment, at least two replaceable batteries are used as the driving power source to supply power to the drive circuit 252. The other components are identical to those shown in FIG. 26. The description of the components will therefore be omitted. The same reference numerals will be assigned to the identical components.

Figure 28:
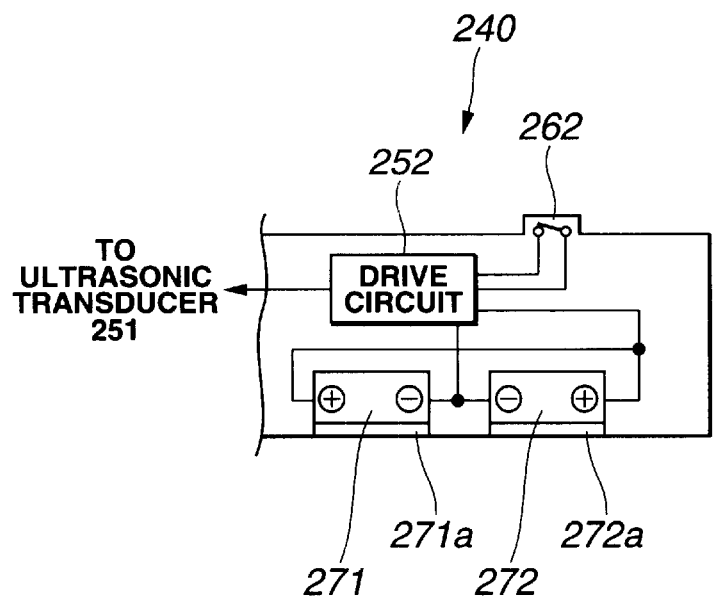
FIG. 28 shows an operation unit for an ultrasonic coagulation/incision instrument in accordance with the thirteenth embodiment of the present invention.

As shown in FIG. 28, two batteries 271 and 272 having lids 271a and 272a, being connected to the drive circuit 252, and capable of being replaced with new ones are incorporated in the operation unit 240 of an ultrasonic coagulation/incision instrument. The battery 271 is placed with a positive electrode thereof located on the left side and a negative electrode thereof located on the right side. The battery 272 is placed with a negative electrode thereof located on the left side and a positive electrode thereof located on the right side. The batteries 271 and 272 are thus connected in parallel with each other.

Consequently, even when one of the two batteries 271 and 272, for example, the battery 271 is removed, driving power can be supplied from the battery 272 to the drive circuit 252.

According to the present embodiment, two batteries that can be removed and renewed are used as a driving power source to supply power to the drive circuit 252. Three or more batteries that can be removed and renewed may be used to supply power to the drive circuit 252.

Fourteenth Embodiment

Next, the fourteenth embodiment of the present invention will be described with reference to FIG. 29.

According to the twelfth and thirteenth embodiments, the ultrasonic coagulation/incision instrument 201 is used to ultrasonically coagulate or incise a living tissue. According to the present embodiment, a bipolar coagulator is used to coagulate a living tissue with high-frequency energy.

Figure 29:
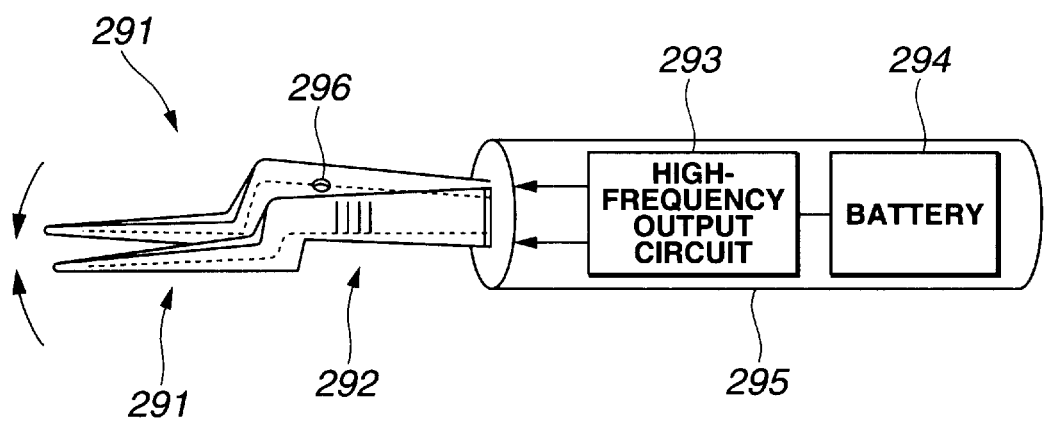
FIG. 29 shows a bipolar coagulator in accordance with the fourteenth embodiment of the present invention.

As shown in FIG. 29, a bipolar coagulator 290 is comprised of a treatment section 291, a hand-held portion 292, and a handpiece 295. The treatment section 291 is used to treat a living tissue. The hand-held portion 292 is located at the proximal end of the treatment section 291 and is a hand-held operating unit by which to manipulate the treatment section 291. A high-frequency output circuit 293 for providing high-frequency energy, and a battery 294 serving as a driving power source for driving the high-frequency output circuit 293 and capable of being renewed are incorporated in the handpiece 295. The bipolar coagulator 290 is a battery-powered treatment instrument having the built-in battery 294 as the driving power source.

A driving switch 296 to be turned on or off by holding the hand-held portion 292 is formed on one side surface of one of two sections of the hand-held portion 292. The hand-held portion 292 is held for clamping a living tissue with the treatment section 291. When the driving switch 296 is thus turned on, power is supplied from the battery 294 to the high-frequency output circuit 293. This causes high-frequency energy, which is used for coagulation, to develop at the treatment section 291. The clamped living tissue is then coagulated with the high-frequency energy.

When the hand-held portion 292 is held, the driving switch 296 is turned on or off responsively. Coagulation is therefore carried out only when needed. Besides, the maneuverability of the treatment instrument improves.

Similarly to the ultrasonic coagulation/incision instrument 201 described in conjunction with FIG. 27, in addition to the driving switch 296, a second switch (not shown) may be formed on the handpiece 295. After the second switch is manually turned on, the hand-held portion 292 may be held to thus turn on the driving switch. In this case, when a living tissue must merely be clamped with the treatment section 291, even if the hand-held portion 292 is held to thus turn on the driving switch 296, coagulation will not be carried out.

Similarly to the ultrasonic coagulation/incision instrument described in conjunction with FIG. 28, at least two batteries capable of being removed may be used as a driving power source to supply power to the high-frequency output circuit 293.

According to the present embodiment, the treatment instrument is of a battery-powered type for performing various kinds of treatment on a living tissue using a battery as a driving power source. The present invention is not limited to this type of treatment instrument. The present invention can also be applied to a treatment instrument in which driving power used to drive the high-frequency output circuit 293 is supplied from an external main unit in order to carry out various kinds of treatment. In this case, for example, after a switch on the external main unit is turned on, the hand-held portion 292 may be held to thus turn on or off the driving switch 296.

Next, a description will be made of a surgical instrument in which an amount of output treatment energy used for treatment is controlled based on a magnitude of holding force with which a hand-held portion is held.

Fifteenth Embodiment

Figure 30:
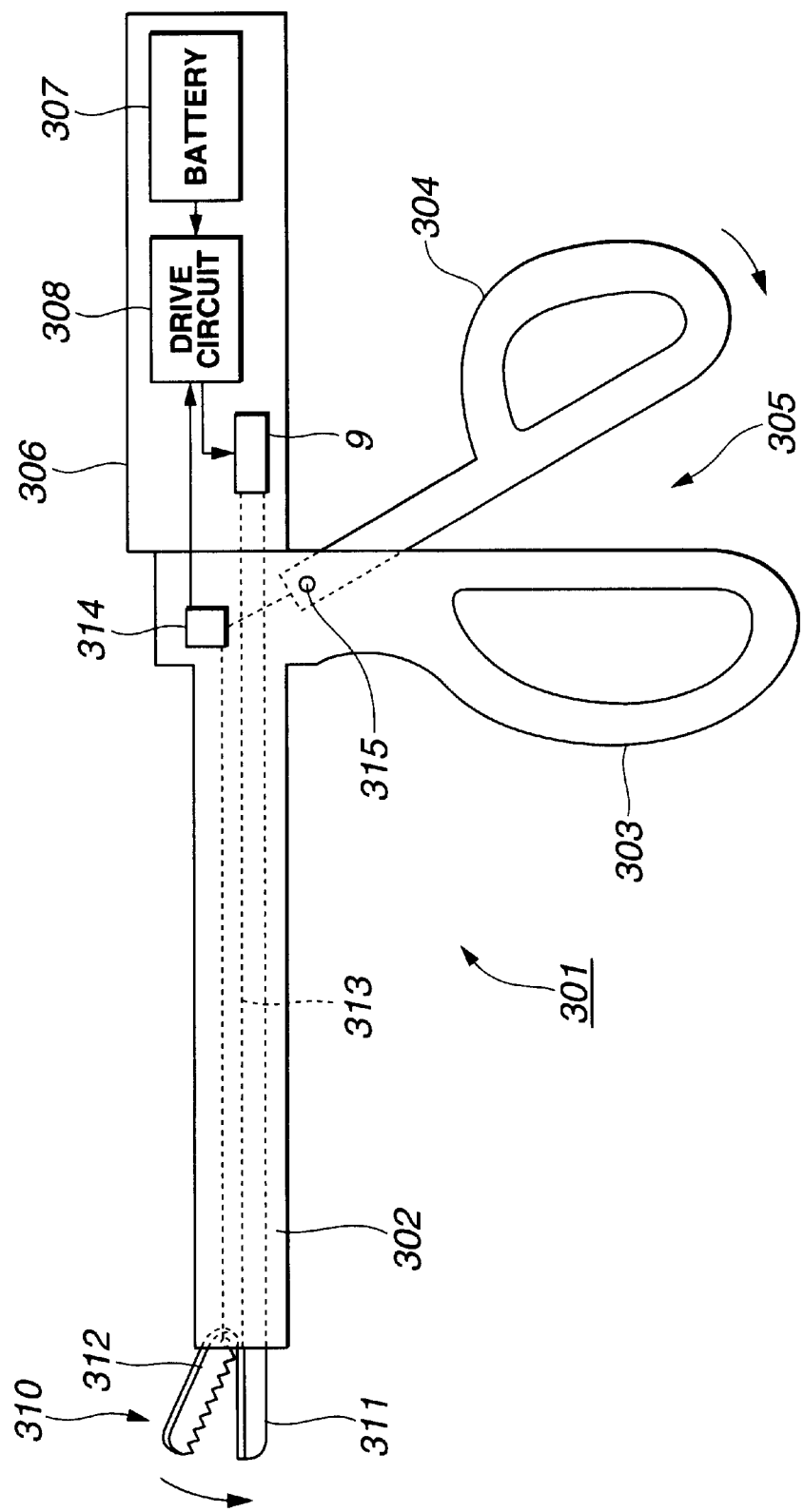
FIG. 30 to FIG. 34 relate to the fifteenth embodiment of the present invention.

As shown in FIG. 30, a battery-powered ultrasonic coagulation/incision instrument 301 in accordance with the fifteenth embodiment consists mainly of an insertion unit 302 and an operation unit 305. The insertion unit 302 is inserted into a body cavity. The operation unit 305 is formed at the proximal end of the insertion unit 302 and composed of a stationary handle 303 and a movable handle 304.

A cylinder 306 is placed along an axis of insertion as a proximal part of the operation unit 305. A secondary battery 307, a drive circuit 308, and an ultrasonic transducer 309 are incorporated in the cylinder 306. Energy to be output from the drive circuit 308 is supplied from the battery 307.

A treatment section 310 is formed at the distal end of the insertion unit 302, and is comprised of a probe 311 and a movable part 312. A drive shaft 313 over which a manipulation performed on the movable handle 304 is conveyed to the movable part 312 extends through the insertion unit 302. A handle 305 is rotatably mounted on a pin 315 extending through stationary handle 303.

The stationary handle 303 has a force detection unit 314 for detecting the magnitude of a force to be propagated to the drive shaft 313. One suitable force detection unit 314 is realized with an electrical capacitance force detector in which the capacitance is a function of the distance between electrodes thereof. Alternatively, a strain gage formed using a piezoelectric element or the like may be used.

Figure 31:
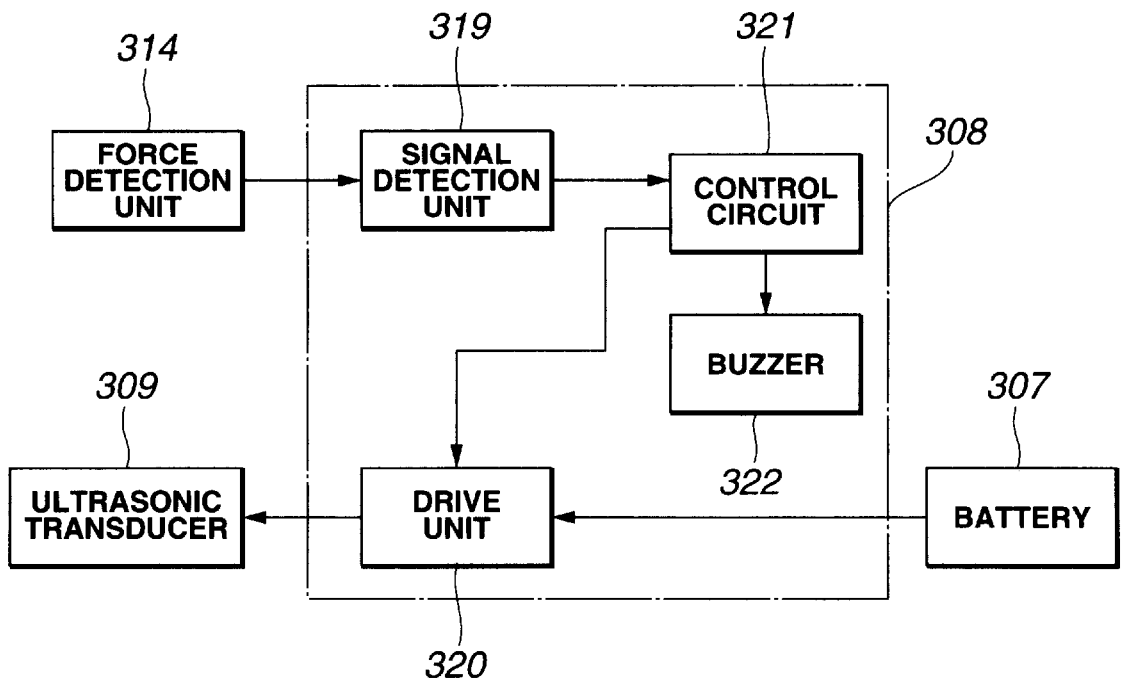

As shown in FIG. 31, the drive circuit 308 consists of a signal detection unit 319, a drive unit 320, a control circuit 321, and a buzzer 322. The signal detection unit 319 detects a signal representing the magnitude of the force detected by the force detection unit 314. The drive unit 320 drives the ultrasonic transducer 309. The control circuit 321 controls the drive unit 320 according to the signal sent from the signal detection unit 319.

The control circuit 321 provides a sound signal to the buzzer 322 according to an amount of energy to be provided to the drive unit 320. The buzzer 322 produces sound whose level is proportional to the voltage level of an output of the drive unit 320 controlled by the control circuit 321.

Figure 32:
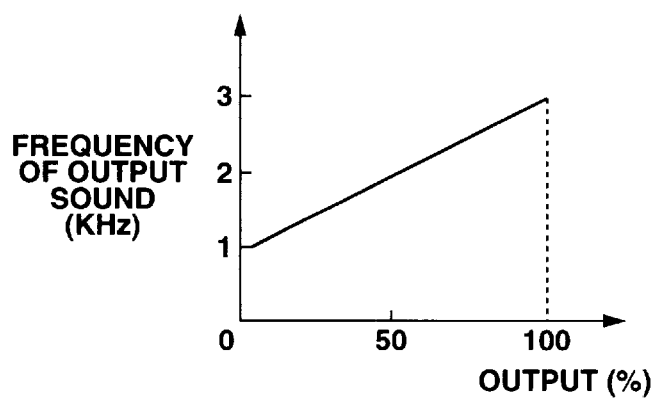

The frequency of the signal provided to buzzer 322 may also vary depending on the amount of output energy. FIG. 32 shows a suitable relationship between the amount of energy output from the control circuit 321 to the drive unit 320 and the frequency of sound output from the buzzer 322.

An operator perceives a change in the frequency of sound output from the buzzer 322 with his/her ears, and thus recognizes a change in the amount of output energy.

Next, a description will be made of operations to be exerted by the battery-powered ultrasonic coagulation/incision instrument 301 in accordance with the present embodiment.

When the battery-powered ultrasonic coagulation/incision instrument 301 is used to coagulate or incise a living tissue, the living tissue is clamped with the probe 311 and movable part 312 of the treatment section 310 by manipulating the movable handle 304. The force detection unit 314 detects the magnitude of clamping force. An output signal of the force detection unit 314 is transmitted to the drive circuit 308. The drive circuit 308 allows the control circuit 321 to control the drive unit 320. Consequently, the ultrasonic transducer 309 is driven with output energy whose amount depends on the output signal of the force detection unit 314.

The relationship between a magnitude of force detected by the force detection unit 314 and the amount of energy output from the drive circuit 308 will be described below.

Assume that a magnitude of force (no-load force) with which the operating unit 305 is moved with nothing clamped is F0(N), and a maximum magnitude of force exerted when the operating unit 305 is gripped is Fmax(N) (constant). When the operation unit 305 is gripped with the maximum magnitude of force, a maximum set amount of energy output from the drive circuit 308 shall be Pmax(W) (constant). Assuming that a magnitude of force detected by the force detection unit 314 when a living tissue is clamped by manipulating the operation unit 305 is F(N), an amount of energy output from the drive circuit 308, P(W), is expressed as follows:

$$P = P\max \times (F-F0)/(F\max - F0)$$

The ultrasonic transducer 309 is driven with the amount of output energy P(W).

In the battery-powered ultrasonic coagulation/incision instrument 301 of the present embodiment, the force detection unit 314 detects a magnitude of force exerted for manipulating the operation unit 305 to clamp a tissue. The control circuit 321 in the drive circuit 308 controls the drive unit 320. The ultrasonic transducer 309 is driven with output energy whose amount depends on an output signal of the force detection unit 314. By manipulating the operation unit 305, a proper amount of output energy can be applied to a tissue from the ultrasonic transducer 309. This obviates the necessity of determining the amount of energy output from the ultrasonic transducer 309 while manipulating the operation unit 305. The maneuverability of the instrument can thus be improved readily and easily.

Figure 33:
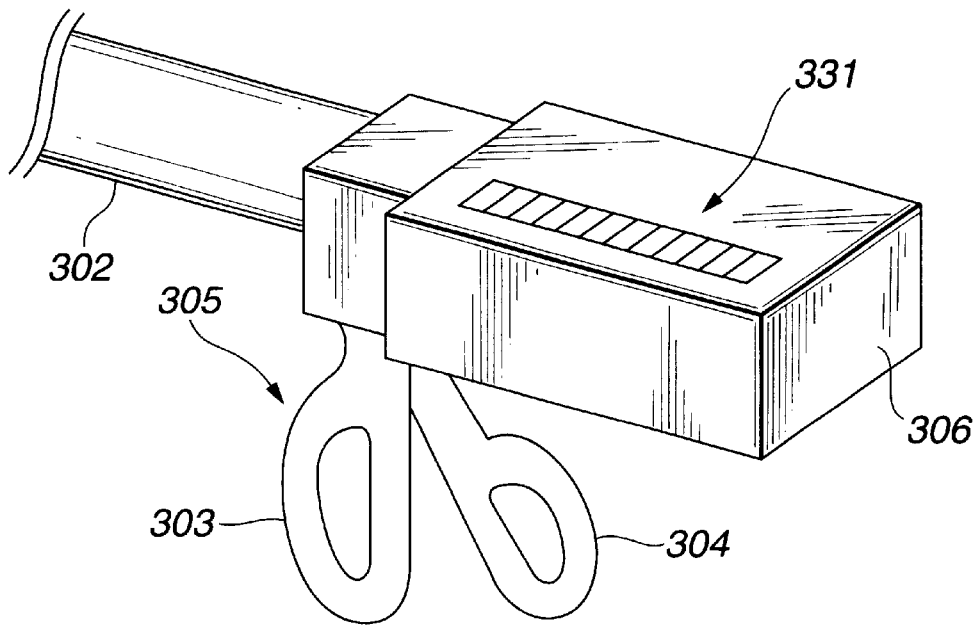

Body portion 306 need not be cylindrical. Instead, it may generally box-shaped as shown on FIG. 33. An indicator 331 composed of LEDs may be formed on the top of the body 306. An amount of energy output from the drive circuit 308 and dependent on a magnitude of force detected by the force detection unit 314 may thus be indicated in the form of a bar. This helps an operator discern an amount of energy indicated with the indicator while performing surgery.

The indicator 331 indicates a ratio of output power to maximum output power (for example, a maximum output is 300 W) as an amount of energy in the form of a bar. Otherwise, the indicator 331 indicates a ratio of the amplitude of ultrasonic waves to a maximum amplitude in the form of a bar.

Figure 34:
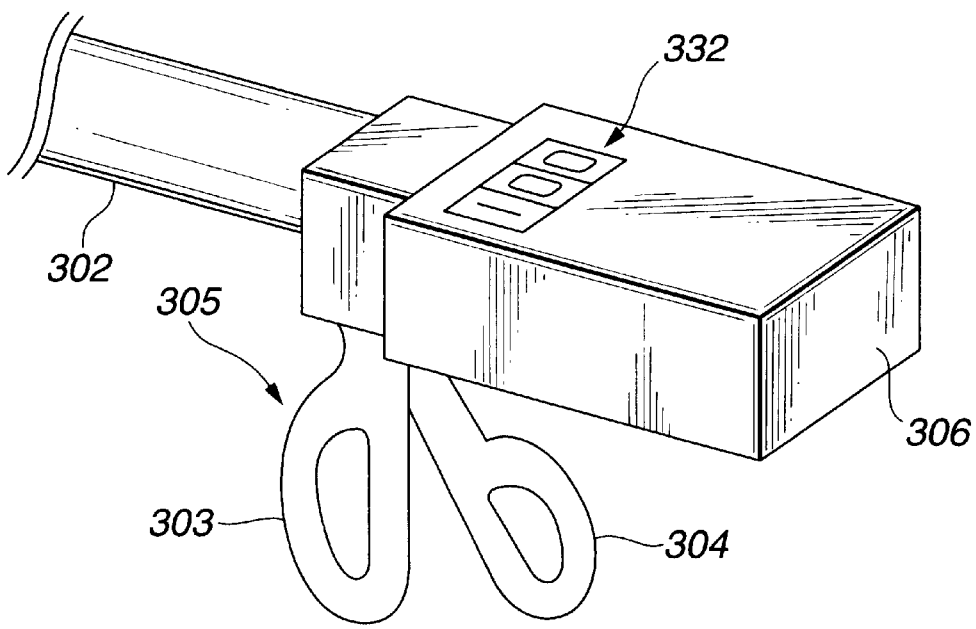

Instead of the indicator 331, a display unit 332 composed of numerical indication LEDs may be provided as shown in FIG. 34, formed on the top of the body 306. In this case, an amount of energy output from the drive circuit 308 according to a magnitude of force detected by the force detection unit 314 is indicated numerically.

Even in this case, an operator can discern an amount of energy displayed on the display unit 332 while performing surgery. Using the display unit 332, output power (in the unit of the watt, for example, a maximum output is 300 W) or the amplitude of ultrasonic waves (a ratio % of the amplitude to a maximum amplitude) is indicated in the form of a numerical value.

Sixteenth Embodiment

Figure 35:
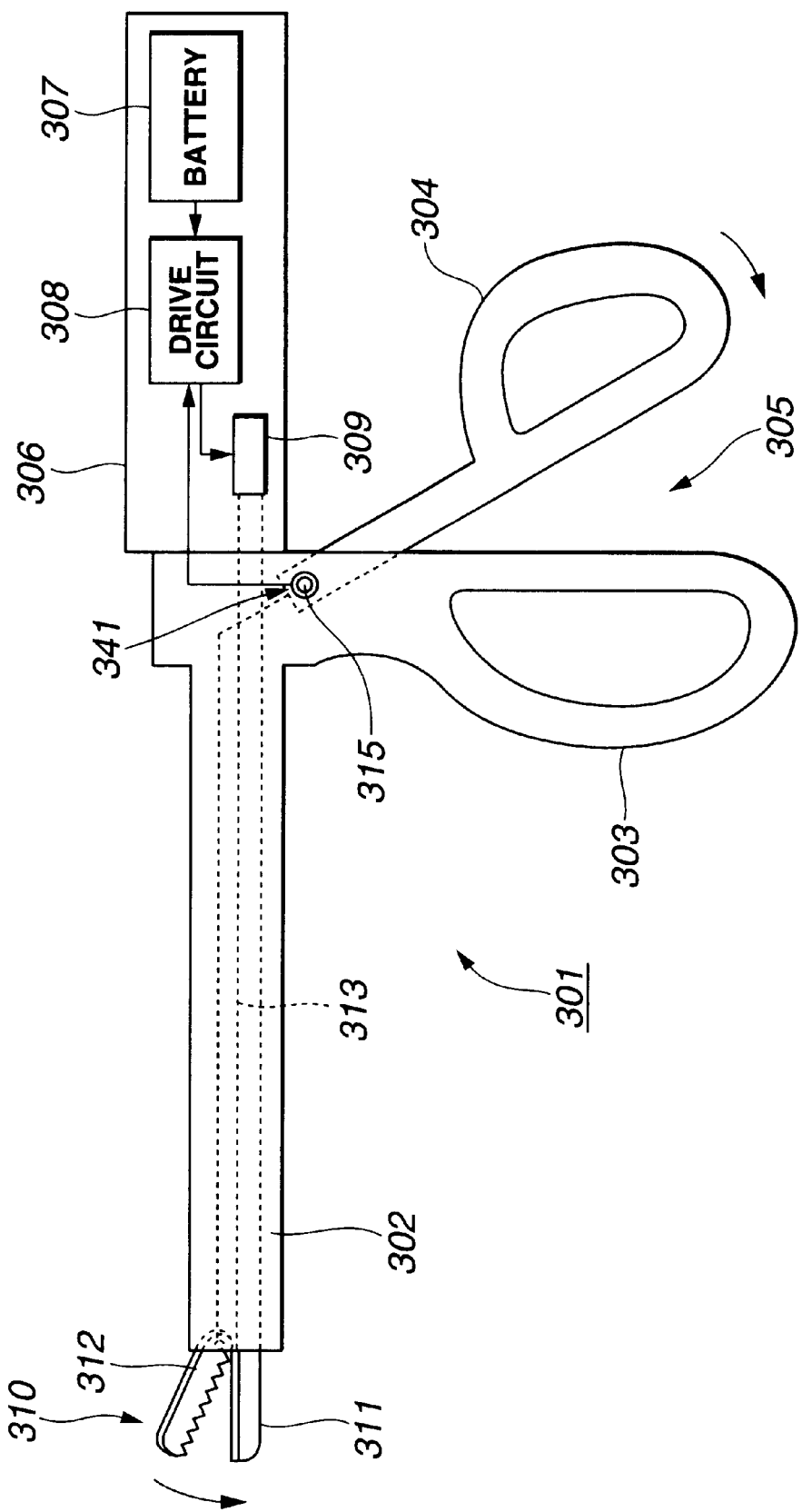
FIG. 35 shows the configuration of a battery-powered ultrasonic coagulation/incision instrument in accordance with the sixteenth embodiment of the present invention.

FIG. 35 shows a battery-powered ultrasonic coagulation/incision instrument 301 in accordance with the sixteenth embodiment of the present invention.

This embodiment differs from the fifteenth embodiment only in that instead of the force detection unit 314, a torque sensor 341 is, as shown in FIG. 35, embedded in the axis 315. Torque applied to the axis 315 is measured.

The torque sensor 341 is formed with a strain gage. An output signal of the torque sensor 341 is transmitted as a magnitude of holding force, with which the movable handle 304 is held, to the drive circuit 308.

The movable handle 305 is manipulated to clamp a tissue with the probe 311 and movable part 312 of the treatment section 310. The torque sensor 341 detects the magnitude of holding force. An output signal from torque sensor 341 is transmitted to the drive circuit 308. The drive circuit 308 drives the ultrasonic transducer 309 with output energy whose amount depends on the output signal.

Next, a surgical instrument having a means for notifying an operator of a driven state of a treatment section will be described below.

Seventeenth Embodiment

Figure 36:
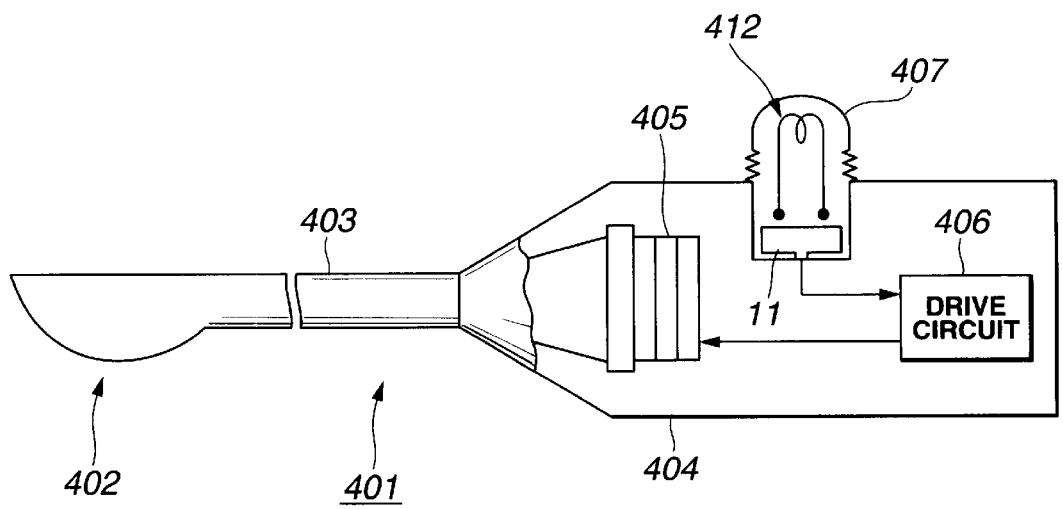

As shown in FIG. 36, a surgical instrument 401 in accordance with the seventeenth embodiment is comprised of an insertion unit 403 and a hand-held portion 404. The insertion unit 403 has a knife section 402, which is a treatment section for incising a tissue, as a distal part thereof. The hand-held portion 404 is located at the proximal end of the insertion unit 403. A transducer 405 for causing the knife section 402 to vibrate, a drive circuit 406 for driving the transducer 405, and a battery unit 407 extending from the top of the hand-held portion 404 for supplying power to the drive circuit 406 are incorporated in the hand-held portion 404.

Figure 37:
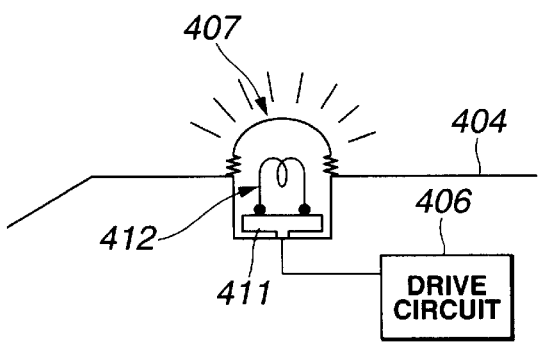

The battery unit 407 consists of a battery 411 formed with a secondary battery utilizing high polymer and serving as a power supplying means, and a light emitter (or LED) 412 serving as a drive acknowledging means. To operate the device shown in FIG. 37, the top of the light emitter 412 is pushed down to the hand-held portion 404. This causes the battery 411 to supply power to the light emitter 412 and drive circuit 406. The light emitter 412 is then lit. The drive circuit 406 drives the transducer 405. Vibrations generated by the transducer 405 are then propagated to the knife section 402.

To be more specific, as shown in FIG. 38A, a contact 422 electrically connected, for example, to a positive electrode of the drive circuit 406, is formed on the inner bottom of a cylindrical screw section 421 of the outer surface of the hand-held portion 404. As illustrated, a first spring 423 made of, for example, copper and conducting electricity to the periphery of the lower surface of the battery 411, constrains the battery 411 to move upward. The first spring 423 is connected to the negative electrode of the drive circuit 406, though it is not shown.

The light emitter such as a miniature bulb 412, is located above battery 411 and is linked to the top of the battery 411 by a second spring 425. A transparent cap 424 is screwed to the screw section 421. The second spring 425 is made of, for example, copper and conducts electricity to the periphery of the top of the battery. The negative electrode of the light emitter 412 that is the side thereof conducts electricity to the second spring 425.

The centers of the upper and lower surfaces of the battery 411 serve as the positive electrode of the battery 411, and the peripheries thereof serve as the negative electrode thereof. The positive and negative electrodes are electrically isolated from each other. When the constraining forces exerted from the first spring 423 and second spring 425 are working, the center of the lower surface of the battery 411 serving as the positive electrode is, as shown in FIG. 38, not meeting the contact 422. Similarly, the center of the upper surface of the battery 411 serving as the positive electrode is not meeting the lower end of the light emitter 412 serving as the positive electrode thereof. In this state, therefore, the light emitter 412 is not lit and the drive unit 406 is not actuated.

When the top of the transparent cap 424 is pushed down, the constraining forces exerted from the first and second springs 423 and 425 are overpowered. The center of the lower surface of the battery 411 serving as the positive electrode meets the contact 422. Likewise, the center of the upper surface of the battery 411 serving as the positive electrode meets the positive electrode of the light emitter 412. In this state, therefore, the light emitter 412 is lit and the drive circuit 406 is actuated.

When the transparent cap 424 is, as shown in FIG. 39, disengaged from the screw section 421, the battery 411 can be renewed.

As mentioned above, according to the present embodiment, when the surgical instrument 401 having the drive circuit 406 driven is in operation, the light emitter 412 that is a drive acknowledgment device lights up. An operator can acknowledge that the surgical instrument 401 is in operation. When the operation of the surgical instrument 401 is stopped, the light emitter 412 is put out. The operator can therefore acknowledge that the surgical instrument 401 has stopped operating.

Eighteenth Embodiment

Figure 40:
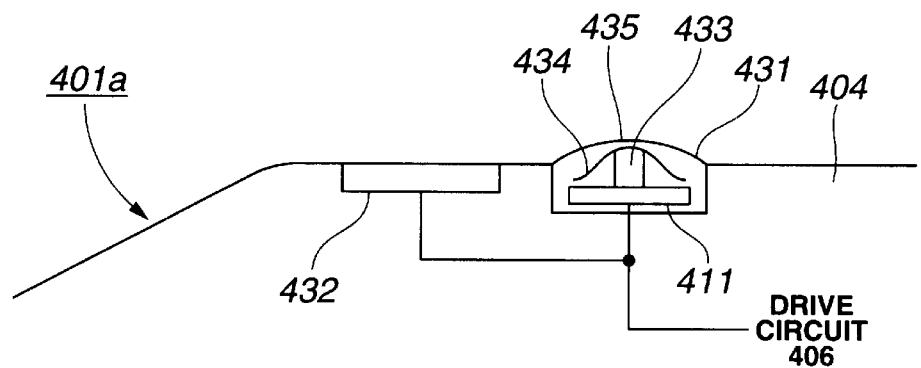
FIG. 40 shows the major configuration of a surgical instrument in accordance with the eighteenth embodiment of the present invention.

FIG. 40 shows a portion of a surgical instrument in accordance with an eighteenth embodiment.

This embodiment is nearly identical to the seventeenth embodiment, differing only in that a hand-held portion 404 of surgical instrument 401a has a switch 431 with a built-in battery 411 and a light-emitting diode (LED) 432 instead of the battery unit 407. The switch 431 has a contact 434. An elastic isolating member 433 is interposed between the contact 434 and the center of the battery 411 serving as the positive electrode thereof. The contact 434 is electrically connected to the drive circuit 406 and the negative electrode of the LED 432, thought it is not shown.

The center of the lower surface of the battery 411 serving as the positive electrode thereof is electrically connected to the drive circuit 406 and the positive electrode of the LED 432. The contact 434 is normally not in contact with the periphery of the battery 411 serving as the negative electrode thereof due to elastic force exerted from the elastic isolating member 433. The contact 434 is therefore normally electrically floating.

When compressing force is applied from the top 435 of the switch 431 to the elastic isolating member 433, the contact 434 meets the negative electrode of the battery 411. Consequently, power is supplied to the LED 432 and drive circuit 406. When the drive circuit 406 is actuated, the LED 432 is lit responsively.

Nineteenth Embodiment

Figure 41:
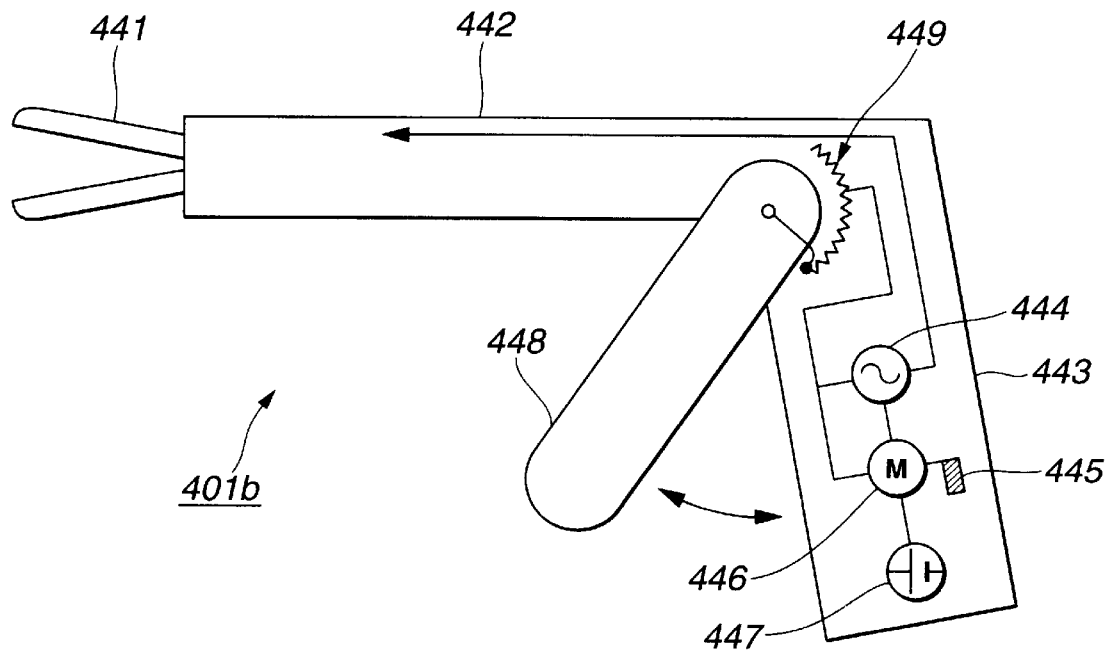
FIG. 41 shows the configuration of a surgical instrument in accordance with the nineteenth embodiment of the present invention.

FIG. 41 shows a surgical instrument in accordance with a nineteenth embodiment of the present invention.

As shown in FIG. 41, a surgical instrument 401b of the present embodiment is comprised of an insertion unit 442 and a hand-held portion 443. The insertion unit 442 is inserted into a body cavity and has a treatment section 441 formed at the distal end thereof. The hand-held portion 443 is formed at the proximal end of the insertion unit 442. An oscillator 444 for supplying energy to the treatment section 441, a motor 446 for rotating an eccentric weight 445 so as to vibrate the hand-held portion 443, and a battery 447 for supplying power to the motor 446 and oscillator 444 are incorporated in the hand-held portion 443.

The output of oscillator 444 is determined by the resistance of a variable resistor 449, the resistance of which depends on a displacement in a turning direction of a handle 448 mounted on the hand-held portion 443. Moreover, when the handle 448 is turned towards the distal part of the surgical instrument 401b opposite to the hand-held portion 443, the variable resistor 449 becomes nonconducting. This disables power supply from the battery 447 to the motor 446 and oscillator 444.

As mentioned above, according to the present embodiment, an output of the treatment section 444 is determined with a displacement made by the handle 448, The hand-held portion 444 is vibrated using the motor 446 according to the output of the treatment section 444. An operator can therefore recognize the output of the treatment section 444.

Surgical apparatuses and surgical instruments in accordance with the present invention are not limited to the aforesaid embodiments. A variety of modifications can be made based on the gist of the present invention.

What is claimed is:

1. A surgical apparatus, comprising:
   a surgical instrument having a rechargeable secondary battery, a treatment section which is electrically driven using the secondary battery and an outer housing for storing the secondary battery and capable of being repeatedly disinfected or sterilized to render the apparatus reusable;
   a recharger having an energy generation unit provided separately from the surgical instrument, for recharging said secondary battery;
   a receiving section provided in the recharger, for receiving the surgical instrument;
   an energy radiation unit provided in the recharger, for converting electric energy from the energy generation unit to energy different from ordinary electric energy and radiating the energy towards the receiving section; and
   a charging energy production unit located in the housing of the surgical instrument, for receiving the energy radiated by the energy radiation unit via the receiving section and the housing and for producing energy with which the secondary battery is recharged,
   wherein the secondary battery can be recharged while it is watertightly stored.

2. A surgical apparatus according to claim 1, wherein said surgical instrument has a detection unit for detecting whether recharging said secondary battery has been completed, and a unit for notifying completion of recharge according to an output of said detection unit.

3. A surgical apparatus according to claim 1, wherein said surgical instrument has a detection unit for detecting whether recharging said secondary battery has been completed; and wherein when said detection unit detects completion of recharge, recharging said secondary battery is stopped.

4. A surgical apparatus according to claim 1, further comprising a separation member that is interposed between said surgical instrument and said energy generation unit, which prevents said surgical instrument from coming in contact with said energy generation unit, while not interrupting propagation of energy from said energy generation unit to said surgical instrument, and which can be washed.

5. A surgical apparatus according to claim 1, further comprising:
   an insertion unit to be inserted into a subject and having said treatment section extending from the distal end thereof;
   a propagation member for propagation driving force to said treatment section;
   an operating unit located at the proximal end of said insertion unit;
   a member freely movable on said operation unit;
   a detection unit for detecting movement of said movable member; and
   a control unit for varying an amount of treatment energy provided from said treatment section according to a signal provided from said detection unit.

6. A surgical apparatus according to claim 1, further comprising:
   an insertion unit to be inserted into a subject and having said treatment section extending from the distal end thereof;
   a propagation member for propagating driving force to said treatment section;
   an operating unit located at the proximal end of said insertion unit;
   a movable member mounted on said operation unit so that it will be freely movable by a predetermined distance;
   a movement detection unit for detecting distance of movement by said movable member; and
   a control unit for varying an amount of treatment energy to be provided from said treatment section according to the movement detected by said movement detection unit.

7. A surgical apparatus according to claim 1, further comprising:
   an insertion unit to be inserted into a subject and having said treatment section extending from the distal end thereof;
   a propagation member for propagating driving force to said treatment section;
   an operating unit located at the proximal end of said insertion unit;
   a member freely movable on said operation unit;
   a moving force detection unit for detecting a magnitude of moving force applied to said movable member; and
   a control unit for varying an amount of treatment energy to be output from said treatment section according to the magnitude of moving force detected by said moving force detection unit.

8. A surgical apparatus according to claim 1, further comprising:
   an insertion unit to be inserted into a subject and having said treatment section extending from the distal end thereof;
   a propagation member for propagating driving force to said treatment section;
   an operating unit located at the proximal end of said insertion unit;
   a member freely movable on said operating unit;
   a movement detection unit for detecting a magnitude of movement made by said movable member; and
   a control unit for varying an amount of treatment energy to be provided from said treatment section according to the magnitude of movement detected by said movement detection unit.

9. A surgical apparatus according to claim 1, further comprising:
   an insertion unit to be inserted into a subject and having said treatment section extending from the distal end thereof;
   an operating unit used to manipulate said treatment section;
   a first switch member for controlling supply of energy to said treatment section; and
   a response unit for giving control to turn on or off said switch member responsively to a manipulation performed on said operating unit.

10. A surgical apparatus according to claim 9, wherein said secondary battery can be renewed.

11. A surgical apparatus according to claim 9, wherein said secondary battery is comprised of a plurality of cells, each of which can be separately renewed.

12. A surgical apparatus according to claim 1, further comprising: a treatment instrument drive unit for driving said treatment section; a switch member for controlling driving of said treatment instrument drive unit; and a driven state annunciator unit for indicating a driven state of said treatment instrument drive unit responsive to a control operation performed by said switch member.

13. A surgical apparatus according to claim 1, wherein said surgical instrument is sealed to have the interior thereof held watertight.

14. A surgical apparatus according to claim 1, wherein said energy generation unit includes a power transmission coil, and said charging energy production unit includes a power reception coil, and wherein the power transmission coil induces current in said power reception coil.

15. A surgical apparatus according to claim 1, further comprising:
   an insertion unit to be inserted into a subject and having said treatment section extending from the distal end thereof;
   the distal part of said treatment section including an implement which applies energy to a tissue for treating the tissue;
   an operating unit to be held for manipulating said treatment section;
   an energy supply unit for supplying energy used for treatment to be performed with said implement;
   a holding force detection unit for detecting a magnitude of holding force with which said operation unit is held;
   a control unit for varying an amount of energy output from said energy supply unit according to the magnitude of holding force detected by said holding force detection unit.

16. A surgical apparatus according to claim 15, further comprising an annunciator unit for helping a user recognize a change in the amount of output energy.

17. A surgical apparatus according to claim 16, wherein said annunciator unit provides an output sound whose level is proportional to an amount of output energy.

18. A surgical apparatus according to claim 16, wherein said annunciator unit is a visual display unit responsive to an amount of output energy.

19. A surgical apparatus according to claim 1, wherein said secondary battery is removably located in a watertight battery chamber.

20. The surgical apparatus according to claim 1, wherein the section for receiving the surgical instrument is a vial that is removably placed on the recharger and the interior of which is maintained in a sterilized condition and which is capable of holding the surgical instrument between uses without contaminating the same.

21. A surgical apparatus, comprising:
a surgical instrument having a rechargeable secondary battery and a treatment section to be electrically driven using said secondary battery, and a capable of being disinfected or sterilized;
an energy generation unit, located outside said surgical instrument, for recharging said secondary battery;
an energy radiation unit, incorporated in said energy generation unit, for radiating energy;
a charging energy production unit, incorporated in said surgical instrument, for receiving the radiated energy without said surgical instrument and said energy generation unit being in electrical contact with each other, and for producing energy with which said secondary battery is recharged; and
wherein said energy generation unit includes a light emission unit, and said charging energy production unit includes a photoelectric conversion unit for receiving light emitted from said light emission unit and photoelectrically converting it.

22. A surgical apparatus, comprising:
a surgical instrument having a rechargeable secondary battery and a treatment section to be electrically driven using said secondary battery, and a capable of being disinfected or sterilized;
an energy generation unit, located outside said surgical instrument, for recharging said secondary battery;
an energy radiation unit, incorporated in said energy generation unit, for radiating energy;
a charging energy production unit, incorporated in said surgical instrument, for receiving the radiated energy without said surgical instrument and said energy generation unit being in electrical contact with each other, and for producing energy with which said secondary battery is recharged;
an insertion unit to be inserted into a subject and having said treatment section extending from the distal end thereof;
an operating unit used to manipulate said treatment section;
a first switch member for controlling supply of energy to said treatment section; and
a response unit for giving control to turn on or off said switch member responsively to a manipulation performed on said operating unit; and
a second switch member, wherein, when said second switch member is turned on and said first switch member is turned on, energy is supplied to said treatment section via an energy supply unit.

23. A surgical apparatus, comprising:
a surgical instrument having a rechargeable secondary battery and a treatment section to be electrically driven using said secondary battery, and a capable of being disinfected or sterilized;
an energy generation unit, located outside said surgical instrument, for recharging said secondary battery;
an energy radiation unit, incorporated in said energy generation unit, for radiating energy;
a charging energy production unit, incorporated in said surgical instrument, for receiving the radiated energy without said surgical instrument and said energy generation unit being in electrical contact with each other, and for producing energy with which said secondary battery is recharged; and
a treatment instrument drive unit for driving said treatment section; a switch member for controlling driving of said treatment instrument drive unit; and an oscillation unit which is controlled based on a driven state of said treatment instrument drive unit.

24. A surgical apparatus, comprising:
a surgical instrument having a rechargeable secondary battery and a treatment section to be electrically driven using said secondary battery, and a capable of being disinfected or sterilized;
an energy generation unit, located outside said surgical instrument, for recharging said secondary battery;
an energy radiation unit, incorporated in said energy generation unit, for radiating energy;
a charging energy production unit, incorporated in said surgical instrument, for receiving the radiated energy without said surgical instrument and said energy generation unit being in electrical contact with each other, and for producing energy with which said secondary battery is recharged; and
wherein said surgical instrument is an ultrasonic surgical instrument having an ultrasonic transducer for generating ultrasonic waves when powered from said secondary battery.

25. A surgical apparatus, comprising:
a surgical instrument having a rechargeable secondary battery and a treatment section to be electrically driven using said secondary battery, and a capable of being disinfected or sterilized;
an energy generation unit, located outside said surgical instrument, for recharging said secondary battery;
an energy radiation unit, incorporated in said energy generation unit, for radiating energy;
a charging energy production unit, incorporated in said surgical instrument, for receiving the radiated energy without said surgical instrument and said energy generation unit being in electrical contact with each other, and for producing energy with which said secondary battery is recharged; and
wherein said surgical instrument is a high-frequency surgical instrument having an oscillator circuit for generating a high-frequency signal when powered from said secondary battery.

* * * * *